US012291570B2

(12) United States Patent
Vainstein-Haras et al.

(10) Patent No.: US 12,291,570 B2
(45) Date of Patent: May 6, 2025

(54) TREATMENT OF METASTATIC PANCREATIC ADENOCARCINOMA

(71) Applicants: BioLineRx Ltd., Modiln (IL); Merck Sharp & Dohme Corp., Rahway, NJ (US)

(72) Inventors: Abi Vainstein-Haras, Herzliya (IL); Ella Sorani, Kadima (IL); Irit Gliko-Kabir, Modiln (IL); Osnat Bohana-Kashtan, Tel-Mond (IL); Amnon Peled, Tel-Aviv (IL)

(73) Assignees: BioLineRx Ltd., Modiln (IL); Merck Sharp & Dohme Corp., Rahway, NJ (US)

( * ) Notice: Subject to any disclaimer, the term of this patent is extended or adjusted under 35 U.S.C. 154(b) by 95 days.

(21) Appl. No.: 17/285,511

(22) PCT Filed: Oct. 17, 2019

(86) PCT No.: PCT/IL2019/051129
§ 371 (c)(1),
(2) Date: Apr. 15, 2021

(87) PCT Pub. No.: WO2020/079692
PCT Pub. Date: Apr. 23, 2020

(65) Prior Publication Data
US 2022/0010016 A1 Jan. 13, 2022

Related U.S. Application Data

(60) Provisional application No. 62/746,587, filed on Oct. 17, 2018.

(51) Int. Cl.
| | | |
|---|---|---|
| C07K 16/28 | (2006.01) | |
| A61K 31/513 | (2006.01) | |
| A61K 38/12 | (2006.01) | |
| A61K 39/00 | (2006.01) | |
| A61K 45/06 | (2006.01) | |
| A61P 35/00 | (2006.01) | |

(52) U.S. Cl.
CPC ........ *C07K 16/2818* (2013.01); *A61K 31/513* (2013.01); *A61K 45/06* (2013.01); *A61P 35/00* (2018.01); *A61K 38/12* (2013.01); *A61K 2039/505* (2013.01); *A61K 2039/545* (2013.01)

(58) Field of Classification Search
CPC ...... A61K 31/513; A61K 45/06; A61K 38/12; A61K 2039/505; A61K 2039/545; A61K 31/4745; A61K 2039/54; A61K 39/3955; A61K 38/10; A61K 31/519; A61K 2300/00; A61P 35/00; A61P 1/18; A61P 35/04; C07K 16/2818
See application file for complete search history.

(56) References Cited

U.S. PATENT DOCUMENTS

| | | | |
|---|---|---|---|
| 7,138,488 B2 | 11/2006 | Fujii | |
| 7,423,007 B2 | 9/2008 | Fujii et al. | |
| 7,595,298 B2 | 9/2009 | Fujii | |
| 8,017,585 B2 | 9/2011 | Fujii et al. | |
| 8,410,059 B2 | 4/2013 | Fujii et al. | |
| 8,765,683 B2 | 7/2014 | Peled et al. | |
| 9,439,942 B2 | 9/2016 | Peled et al. | |
| 10,682,390 B2 * | 6/2020 | Peled | A61K 38/1761 |
| 10,786,547 B2 | 9/2020 | Peled et al. | |
| 11,534,478 B2 * | 12/2022 | Peled | C07K 16/30 |
| 11,554,159 B2 | 1/2023 | Peled et al. | |
| 11,559,562 B2 * | 1/2023 | Peled | A61K 47/646 |
| 11,590,200 B2 | 2/2023 | Peled et al. | |
| 11,599,666 B2 | 3/2023 | Nayak | |
| 11,607,444 B2 | 3/2023 | Peled et al. | |
| 11,612,638 B2 | 3/2023 | Peled et al. | |
| 11,638,742 B2 | 5/2023 | Peled et al. | |
| 11,638,743 B2 | 5/2023 | Peled et al. | |
| 11,642,393 B2 | 5/2023 | Peled et al. | |
| 11,648,293 B2 | 5/2023 | Peled et al. | |
| 2006/0264378 A1 | 11/2006 | Fujii et al. | |
| 2020/0223924 A1 | 7/2020 | Stein et al. | |
| 2022/0072087 A1 | 3/2022 | Stein et al. | |
| 2023/0242644 A1 | 8/2023 | Vainstein-Haras et al. | |
| 2024/0082348 A1 | 3/2024 | Halbfinger et al. | |

FOREIGN PATENT DOCUMENTS

| | | | |
|---|---|---|---|
| CN | 108026173 | 5/2018 | |
| CN | 108495629 | 9/2018 | |
| WO | WO 2013/188586 | 12/2013 | |
| WO | WO 2017/ 034957 | * 8/2016 | A61K 31/436 |
| WO | WO 2017/009842 | 1/2017 | |

(Continued)

OTHER PUBLICATIONS

Weiss G et al., Phase Ib/II study of gemcitabine, nab-paclitaxel, and pembrolizumab in metastatic pancreatic adenocarcinoma, 2017, Investigational New Drugs, 36:96-102 (Year: 2017).*
Hadzijusufovic E et al., H1-receptor antagonists terfenadine and loratadine inhibit spontaneous growth of neoplastic mast cells, 2010, Experimental Hematology, 38:896-907 (Year: 2010).*
Gandhi L et al., Pembrolizumab plus Chemotherapy in Metastatic Non-Small-Cell Lung Cancer, 2018, NEJM, 378;22 (Year: 2018).*
Clinical trial#NCT02826486, 2016, https://clinicaltrials.gov/ct2/show/record/NCT02826486.*
Wang-Gillam et. al., Lancet. 387:545-557 (2016) (Year: 2016).*
Kim et. al. PLOS Computational Biology. 12(3):1-15. (2016) (Year: 2016).*
Deer et. al. Pancreas 39(4).425-435. (2011) (Year: 2011).*
Wang et. al. Current Cancer Drug Targets 14:407-417 (2014) (Year: 2014).*

(Continued)

*Primary Examiner* — Meera Natarajan
*Assistant Examiner* — Francesca Edgingtongiordano

(57) ABSTRACT

A method of treating metastatic pancreatic adenocarcinoma in a subject in need thereof is provided. The method comprising administering to the subject a therapeutically effective amount of each of a peptide set forth in SEQ ID NO: 1, an anti PD-1 and a chemotherapy, thereby treating the metastatic pancreatic adenocarcinoma.

11 Claims, 1 Drawing Sheet

Specification includes a Sequence Listing.

(56) References Cited

FOREIGN PATENT DOCUMENTS

| WO | WO 2017/009843 | 1/2017 |
|---|---|---|
| WO | WO 2018/083470 | 5/2018 |
| WO | WO 2020/079692 | 4/2020 |
| WO | WO 2020/148744 | 7/2020 |
| WO | WO 2020/148745 | 7/2020 |
| WO | WO 2021/009761 | 1/2021 |

OTHER PUBLICATIONS

BioLineRx Announces Final Results from Phase 2a Combat/Keynote-202 Triple Combination Study of Motixafortide in Second Line Metastatic Pancreatic Cancer (PDAC) (2020) (Year: 2020).*
Mercadé et. al. (Pancreas 49(1):62-75. (2020)) (Year: 2020).*
Petrelli et. al. European Journal of Cancer. 81:174-182 (2017) (Year: 2017).*
Wang-Gilliam et. al. (European Journal of Cancer 108:78-87 (2019) (Year: 2019).*
Tourneua et. al. JNCI. 101(10):708-720. 2009 (Year: 2009).*
Bockorny et. al. Nat Med. 26:878-885 (2020) (Year: 2020).*
International Preliminary Report on Patentability Dated Apr. 29, 2021 From the International Bureau of WIPO Re. Application No. PCT/IL2019/051129. (8 Pages).
International Search Report and the Written Opinion Dated Oct. 21, 2020 From the International Searching Authority Re. Application No. PCT/IL2020/050798. (13 Pages).
International Search Report and the Written Opinion Dated Feb. 26, 2020 From the International Searching Authority Re. Application No. PCT/IL2019/051126. (16 Pages).
International Search Report and the Written Opinion Dated Feb. 26, 2020 From the International Searching Authority Re. Application No. PCT/IL2019/051129. (16 Pages).
International Search Report and the Written Opinion Dated Feb. 26, 2020 From the International Searching Authority Re. Application No. PCT/IL2019/051127. (16 Pages).
Beider et al. "Anti-Leukemia and Multiple Myeloma Selective Activity of CXCR4 Antagonist 4F-Benzoyl-TN14003 Involves Apoptotic Death Pathway", Database BIOSIS [Online], XP002796778, Database Accession No. PREV201000354849, 3 P., Nov. 20, 2009.
Beider et al. "Anti-Leukemia and Multiple Myeloma Selective Activity of CXCR4 Antagonist 4F-Benzoyl-TN14003 Involves Apoptotic Death Pathway", XP882796778, Blood, 114(22): 3857, Nov. 20, 2009.
Gebbia et al. "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale", American Journal of Clinical Oncology, XP055461997, 33(5): 461-464, Oct. 2010.
Hidalgo et al. "Evaluation of Pharmacodynamic (PD) Biomarkers in Patients With Metastatic Pancreatic Cancer Treated With BL-8040, A Novel CXCR4 Antagonist", Journal of Clinical Oncology, 36(5/Suppl.): # 88, Feb. 10, 2018.
Kim et al. "Comprehensive Review of PD1/L1 Inhibition in Metastatic Solid Tumors: Safety, Efficacy and Resistance", XP055659482, Journal of Biomedical Sciences, 6(2:14): 1-9, Feb. 22, 2017.
Mori et al. "Involvement of Stromal Cell-Derived Factor 1 and CXCR4 Receptor System in Pancreatic Cancer", Gastroenterology, XP009021758, 122(4/Suppl.1): A490, Abstract # T1608, Apr. 2002.
Smith et al. "Nivolumab for the Treatment of Colorectal Cancer",Expert Review of Anticancer Therapy, 18(7): 611-618, Jun. 11, 2018.
ClinicalTrials "Chemo4METPANC Combination Chemotherapy in Patients With Pancreatic Adenocarcinoma", History of Changes for Study: NCT04543071, Nov. 7, 2022.
International Preliminary Report on Patentability Dated Jul. 29, 2021 From the International Bureau of WIPO Re. Application No. PCT/IL2019/051127. (8 Pages).
Office Action Dated Jul. 20, 2023 From the Israel Patent Office Re. Application No. 282317. (4 Pages).
Notification of Office Action and Search Report Dated Dec. 1, 2023 From the National Intellectual Property Administration of the People's Republic of China Re. Application No. 201980081755.X. (6 Pages).
Notice of Reason(s) for Rejection Dated Sep. 5, 2023 From the Japan Patent Office Re. Application No. 2021-519139. (3 pages).
Weiss et al. "A Phase Ib Study of Pembrolizumab Plus Chemotherapy in Patients With Advanced Cancer (PembroPlus)", British Journal of Cancer, 117(1): 33-40, 2017.
English Translation Dated Dec. 12, 2023 of Notification of Office Action and Search Report Dated Dec. 1, 2023 From the National Intellectual Property Administration of the People's Republic of China Re. Application No. 201980081755.X. (3 Pages).
Translation Dated Sep. 19, 2023 of Notice of Reason(s) for Rejection Dated Sep. 5, 2023 From the Japan Patent Office Re. Application No. 2021-519139. (4 pages).
Communication Pursuant to Article 94(3) EPC Dated Mar. 7, 2024 From the European Patent Office Re. Application No. 19797388.6 (6 Pages).
Restriction Official Action Dated Mar. 1, 2024 From the US Patent and Trademark Office Re. U.S. Appl. No. 17/422,786. (8 pages).
Translation Dated Mar. 1, 2024 of Notice of Reason(s) for Rejection Dated Feb. 20, 2024 From the Japan Patent Office Re. Application No. 2021-519139. (1 page).
Official Action Dated Apr. 30, 2024 from the US Patent and Trademark Office Re. U.S. Appl. No. 7/422,786. (86 pages).
Official Action Dated Mar. 8, 2024 From the US Patent and Trademark Office Re. U.S. Appl. No. 18/109,281. (36 pages).
Berlin et al. "Editorial: Combined Modality Treatment of Resectable and Borderline Resectable Pancreas Cancer: Expert Consensus Conference", Annals of Surgical Oncology, 16: 1757-1759, 2009.
Notice of Reason(s) for Rejection Dated Feb. 20, 2024 From the Japan Patent Office Re. Application No. 2021-519139. (3 pages).
Examination Report Dated Nov. 7, 2024 From the Australian Government, IP Australia Re. Application No. 2019360044. (4 Pages).
Communication Pursuant to Article 94(3) EPC Dated May 22, 2024 From the European Patent Office Re. Application No. 19797831.5. (5 Pages).
Examination Report Dated Jul. 22, 2024 From the Australian Government, IP Australia Re. Application No. 2019360044. (5 Pages).
Official Action Dated Jun. 18, 2024 from the US Patent and Trademark Office Re. U.S. Appl. No. 18/109,281. (29 pages).
Official Action Dated Feb. 26, 2025 from the US Patent and Trademark Office Re. U.S. Appl. No. 18/109,281. (24 pages).
Feig et al. "Targeting CXCL12 from FAP-expressing Carcinoma-associated Fibroblasts Synergizes with Anti-PD-L1 Immunotherapy in Pancreatic Cancer", Research Article, Biological Sciences, PNAS, 110 (50) 20212-20217, Nov. 25, 2013.
Manji et al. "CheMo4METPANC: A Randomized Phase 2 Study with Combination Chemotherapy (Gemcitabine and Nab-paclitaxel), Chemokine (C-X-C) Motif Receptor 4 Inhibitor (Motixafortide), and Immune Checkpoint Blockade (Cemiplimab) Compared to Chemotherapy Alone in Metastatic Treatment-naïve Pancreatic Adenocarcinoma", Journal of Clinical Oncology, vol. 42, No. 16_suppliment TPS4208, May 29, 2024.

* cited by examiner

TREATMENT OF METASTATIC PANCREATIC ADENOCARCINOMA

RELATED APPLICATION/S

This application is a National Phase of PCT Patent Application No. PCT/IL2019/051129 having International filing date of Oct. 17, 2019, which claims the benefit of priority under 35 USC § 119(e) of U.S. Provisional Patent Application No. 62/746,587 filed on Oct. 17, 2018. The contents of the above applications are all incorporated by reference as if fully set forth herein in their entirety.

SEQUENCE LISTING STATEMENT

The ASCII file, entitled 87325Sequence-Listing.txt, created on Apr. 15, 2021, comprising 1018 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods and uses of agents for the treatment of metastatic pancreatic adenocarcinoma.

Cancer immunotherapy, a novel and rapidly growing field of research, investigates the use of therapies that harness the body's own immune system in the fight against cancer. Tumors utilize a variety of mechanisms to evade host immune detection. There is mounting evidence that tumor-infiltrating immune cells such as myeloid-derived suppressor cells (MDSCs), regulatory T cells (Tregs) and tumor-associated macrophages, actively modulate the tumor microenvironment to suppress the effector arms of this response. The aim of the cancer immunotherapy approach is to prevent the tumor's ability to suppress its own detection and elimination by the host immune system. A number of biologic agents that target a range of immune signaling mechanisms, e.g., programmed-death receptor 1 (PD-1)/programmed-death receptor ligand 1 (PD-L1), Lymphocyte-activation gene 3 (LAG-3), and killer-immunoglobulin-like receptor (KIR), are in clinical development for the treatment of a variety of cancers. However, a fraction of subjects do not respond to these therapies as a result of local immunosuppression mediated by stromal cells (mostly fibroblasts). It was found that activated fibroblasts in the tumor stroma mediate immune suppression in several mouse models of cancer. One suggestion for the basis of the immune suppression involves the production of the chemokine, CXCL12, by the fibroblastic stromal cells. Binding of CXCL12 by T cells leads to their exclusion from the vicinity of the cancer cells. T cell exclusion causes antagonists of T cell checkpoints to be ineffective, despite the presence of cancer-specific CD8+ T cells. Preclinical studies have demonstrated that this immune suppression is interrupted by administration of inhibitors of CXC chemokine receptor 4 (CXCR4), the receptor for CXCL12, which leads to the rapid accumulation of T cells among cancer cells, thereby uncovering the efficacy of immune checkpoints inhibitors.

BL-8040

BL-8040 (previously named BKT140, SEQ ID NO: 1) is a highly selective CXCR4 antagonist. The investigational drug is a 14-residue, cyclic, synthetic peptide capped with an aromatic ring that binds to CXCR4 with high affinity ($IC_{50}$ 0.54-4.5 nM) and inhibits its function[1]. The chemokine CXCL12 (SDF-1-stromal-derived-factor-1) and its receptor, CXCR4, play a pivotal role in the trafficking of hematopoietic cells to the bone marrow (BM)[2]. Animal studies exploring the activity of BL-8040 in various cancer models in mice have shown that in addition to its activity as a mobilizer of hematopoietic cells, BL-8040 exhibits a CXCR4-dependent preferential antitumor effect against malignant cells overexpressing CXCR4[3]. The efficacy of BL-8040 and its analogs for blocking CXCR4 in vitro and in vivo has been documented in numerous preclinical studies, including in vitro and in vivo models for small cell lung carcinoma, breast cancer, malignant melanoma, neuroblastoma and pancreatic cancer. As a CXCR4 antagonist, BL-8040 also affects the trafficking of immune cells to the tumor microenvironment. It was found that administration of BL-8040 induces the mobilization of Natural Killer (NK) cells, T cells and B cells from the BM and lymph nodes into the periphery. Using a syngeneic cancer model in mice it was demonstrated that BL-8040 may eliminate the immunological barrier and allow the accumulation of immune cells within the tumor microenvironment.

Preclinical Studies

The nonclinical development of BL-8040 has encompassed a large number of pharmacodynamic, pharmacokinetic (PK), safety pharmacology, and single and repeated dose toxicity studies.

BL-8040 exhibits CXCR4-dependent selective cytotoxicity toward malignant cells both in vivo and in vitro and induces apoptotic cell death in cancer cells[3-6]. BL-8040 leads to phosphatidylserine externalization, decreased mitochondrial membrane potential, caspase activation, subsequent sub-G1 arrest and DNA double-stranded breaks in leukemic and multiple myeloma cells [3]. These effects were shown to be specific; BL-8040 did not affect the viability of human keratinocytes and normal human hematopoietic cells [3]. This property of direct apoptotic effects on top of the mobilization capacity, distinguishes BL-8040 from other CXCR4 antagonists agents such as Mozobil/Plerixafor [3]. In addition, administration of BL-8040 induces the mobilization of NK cells, T cells and B cells from the BM and lymph nodes into the periphery.

BL-8040 has demonstrated safety and initial clinical efficacy in several Phase I and II studies [Hidalgo M M, Epelbaum R, Semenisty V, Geva R, Golan T, Borazanci E H. Evaluation of pharmacodynamic (PD) biomarkers in patients with metastatic pancreatic cancer treated with BL-8040, a novel CXCR4 antagonist. J Clin Oncol. 2018; 36:88-88. Abstract].

Pembrolizumab

Pembrolizumab is a potent humanized immunoglobulin G4 (IgG4) monoclonal antibody (mAb) with high specificity of binding to the PD-1 receptor, thus inhibiting its interaction with PD-L1 and PD-L2. Based on preclinical in vitro data, pembrolizumab has high affinity and potent receptor blocking activity for PD-1. Pembrolizumab has an acceptable preclinical safety profile and is in clinical development as an IV immunotherapy for advanced malignancies. Keytruda® (pembrolizumab) is indicated for the treatment of patients across a number of indications.

Pharmaceutical and Therapeutic Background

The importance of intact immune surveillance function in controlling outgrowth of neoplastic transformations has been known for decades [7]. Accumulating evidence shows a correlation between tumor-infiltrating lymphocytes in cancer tissue and favorable prognosis in various malignancies. In particular, the presence of CD8+ T cells and the ratio of CD8+ effector T-cells/FoxP3+ regulatory T cells (Tregs) correlates with improved prognosis and long-term survival in solid malignancies, such as ovarian, colorectal, and pancreatic cancer; hepatocellular carcinoma; malignant melanoma; and renal cell carcinoma. Tumor-infiltrating lymphocytes can be expanded ex vivo and reinfused, inducing durable objective tumor responses in cancers such as melanoma[8,9].

The PD-1 receptor-ligand interaction is a major pathway hijacked by tumors to suppress immune control. The normal function of PD-1, expressed on the cell surface of activated T-cells under healthy conditions, is to down-modulate unwanted or excessive immune responses, including autoimmune reactions. PD-1 (encoded by the gene Pdcd1) is an immunoglobulin (Ig) superfamily member related to cluster of differentiation 28 (CD28) and cytotoxic T-lymphocyte-associated protein 4 (CTLA-4) that has been shown to negatively regulate antigen receptor signaling upon engagement of its ligands (PD-L1 and/or PD-L2)[10,11].

The structure of murine PD-1 has been resolved[12]. PD-1 and its family members are type I transmembrane glycoproteins containing an Ig-variable-type (IgV-type) domain responsible for ligand binding and a cytoplasmic tail responsible for the binding of signaling molecules. The cytoplasmic tail of PD-1 contains 2 tyrosine-based signaling motifs, an immunoreceptor tyrosine-based inhibition motif, and an immunoreceptor tyrosine-based switch motif. Following T cell stimulation, PD-1 recruits the tyrosine phosphatases, SHP-1 and SHP-2, to the immunoreceptor tyrosine-based switch motif within its cytoplasmic tail, leading to the dephosphorylation of effector molecules such as CD3 zeta (CD3), protein kinase C-theta (PKCθ), and zeta-chain-associated protein kinase (ZAP70), which are involved in the CD3 T cell signaling cascade[11,13-15]. The mechanism by which PD-1 down-modulates T-cell responses is similar to, but distinct from, that of CTLA-4, because both molecules regulate an overlapping set of signaling proteins[16, 17]. As a consequence, the PD-1/PD-L1 pathway is an attractive target for therapeutic intervention in pancreatic cancer.

Preclinical and Clinical Trials

Therapeutic studies in mouse models have shown that administration of antibodies blocking PD-1/PD-L1 interaction enhances infiltration of tumor-specific CD8+ T cells and ultimately leads to tumor rejection, either as a monotherapy or in combination with other treatment modalities [18-23]. Anti-mouse PD-1 or anti-mouse PD-L1 antibodies have demonstrated antitumor responses in models of squamous cell carcinoma, pancreatic carcinoma, melanoma, AML and colorectal carcinoma[12,22-25]. In such studies, tumor infiltration by CD8+ T cells and increased IFN-γ, granzyme B and perforin expression were observed, indicating that the mechanism underlying the antitumor activity of PD-1 checkpoint inhibition involved local infiltration and activation of effector T cell function in vivo [22]. Experiments have confirmed the in vivo efficacy of anti-mouse PD-1 antibody as a monotherapy, as well as in combination with chemotherapy, in syngeneic mouse tumor models (see the pembrolizumab IB).

Chemotherapy: Nanoliposomal Irinotecan with Fluorouracil and Leucovorin (Onivyde® with 5-FU/LV)

Liposomal irinotecan is a liposome-encapsulated formulation of the topoisomerase-1 inhibitor irinotecan, developed to overcome the pharmacological and clinical limitations of non-liposomal irinotecan[26,27]. 5-FU is a nucleoside metabolic inhibitor indicated for the treatment of patients with pancreatic adenocarcinoma[28]. LV is a chemically-reduced derivative of folic acid. It can enhance the therapeutic and toxic effects of 5-FU. Concurrent administration of LV does not appear to alter the plasma pharmacokinetics of 5-FU. 5-FU is metabolized to fluorodeoxyuridylic acid, which binds to and inhibits the enzyme thymidylate synthase (an enzyme important in DNA repair and replication). LV is readily converted to another reduced folate, 5,10-methylenetetrahydrofolate, which acts to stabilize the binding of fluorodeoxyuridylic acid to thymidylate synthase and thereby enhances the inhibition of this enzyme[29]. IV liposomal irinotecan injection (Onivyde®) is approved for use in combination with 5-FU and LV (5-FU/LV) in patients with metastatic pancreatic adenocarcinoma that has progressed following gemcitabine-based therapy. In the pivotal multinational, phase III NAPOLI-1 trial in patients with metastatic pancreatic adenocarcinoma that had progressed following gemcitabine-based therapy, liposomal irinotecan in combination with 5-FU/LV significantly prolonged median Overall Survival (OS) (primary endpoint) and median progression-free survival (PFS) at the time of the primary analysis (after 313 events) and final analysis (after 382 events) compared with 5-FU/LV control therapy. The objective response rate (ORR) was also significantly higher in the liposomal irinotecan plus 5-FU/LV group than in the control group. Liposomal irinotecan-based combination therapy had a manageable safety profile; the most common TEAEs of Grade 3 severity were hematological or gastrointestinal in nature[26,27].

Therapeutic Indication

Pancreatic cancer is a malignant neoplasm of the pancreas with a low early-diagnosis rate and poor prognosis. Its incidence rate has risen in recent years and it now comprises 1%-2% of common tumors. Each year about 185,000 individuals globally are diagnosed with this condition. As its symptoms are usually non-specific, pancreatic cancer is often not diagnosed until it reaches an advanced stage. The only potentially curative therapy for pancreatic cancer is surgical resection. Unfortunately, tumors in only 20% patients are resectable at the time of diagnosis. Even among those patients who undergo resection for pancreatic cancer and have tumor-free margins, the 5-year survival rate is only 10%-25%[30,31]. The overall 5-year survival rate among patients is less than 5%, which constitutes the highest mortality rates among solid malignancies. The overall median survival is less than 1 year from diagnosis, highlighting the need for the development of newer therapeutic options.

The anatomical structure of the pancreas is very complicated. The high interstitial tension and inadequate blood perfusion of the pancreatic tumors give them extreme resistance to most chemotherapy drugs. Consequently, conventional systemic IV chemotherapy often fails to reach effective concentrations. High dosages may cause severe adverse reactions, thus impairing the immune system and reducing the potential therapeutic effect. The failure of clinical treatment in patients with pancreatic ductal adenocarcinoma is often attributed to the early metastatic growth, a high level of drug resistance to standard therapy options and high rates of local recurrence[32].

Despite recent advances in chemotherapeutics and in the understanding of the molecular biology of pancreatic cancer, there has been limited progress in therapeutic options for metastatic disease. Over the past four decades, studies of several combination therapies have demonstrated minimal or no survival benefit compared with gemcitabine alone. Gemcitabine monotherapy had been the standard of care for patients with metastatic pancreatic cancer for several years, until combination therapy with gemcitabine plus erlotinib was shown to increase median survival by 2 weeks. However, the modest survival benefit was tempered by a significant side effect profile and the high cost of treatment. Later, the multidrug combination of LV, 5-FU, irinotecan, and oxaliplatin (FOLFIRINOX) showed an increased median survival of 4.3 months; however, given its side effect profile, it is available only to a select group of patients with advanced pancreatic cancer. Recently, the gemcitabine plus nab-paclitaxel combination was shown to increase median survival by 1.8 months, with increased OS at 1 and 2 years; AEs were reasonable; they included cytopenias and peripheral neuropathy[33]. The current National Comprehensive Cancer Network recommendations suggest acceptable chemotherapy combinations for patients with good performance status (i.e., ECOG performance status of 0 or 1), good pain management, patent biliary stent, and adequate nutritional intake; these combinations include FOLFIRINOX, gemcitabine plus nab-paclitaxel, and gemcitabine plus erlotinib. The only recommended option for patients with poor performance status is gemcitabine monotherapy. In 2015, Onivyde® was the first chemotherapeutic agent approved in the US and in the EU in combination with 5-FU and LV, for the treatment of patients with metastatic adenocarcinoma of the pancreas in second line settings, after disease progression following gemcitabine-based therapy [26,34].

Additional background art includes:
WO2017009843
WO2017009842.

SUMMARY OF THE INVENTION

According to an aspect of some embodiments of the present invention there is provided a method of treating metastatic pancreatic adenocarcinoma in a subject in need thereof, the method comprising administering to the subject a therapeutically effective amount of each of a peptide set forth in SEQ ID NO: 1, an anti PD-1 and a chemotherapy, thereby treating the metastatic pancreatic adenocarcinoma.

According to an aspect of some embodiments of the present invention there is provided a therapeutically effective amount of each of a peptide set forth in SEQ ID NO: 1, an anti PD-1 and a chemotherapy for use in treating metastatic pancreatic adenocarcinoma in a subject in need thereof.

According to an aspect of some embodiments of the present invention there is provided an article of manufacture comprising a therapeutically effective amount of each of a peptide set forth in SEQ ID NO: 1, an anti PD-1 and a chemotherapy for use in the treatment of metastatic pancreatic adenocarcinoma.

According to some embodiments of the invention, the anti PD-1 is pembrolizumab.

According to some embodiments of the invention, the chemotherapy comprises a plurality of chemotherapeutic agents.

According to some embodiments of the invention, the chemotherapy comprises irinotecan, fluorouracil (5-FU) and leucovorin (LV).

According to some embodiments of the invention, the irinotecan is liposome-encapsulated.

According to some embodiments of the invention, the irinotecan is Onivyde®.

According to some embodiments of the invention, the peptide is administered subcutaneously (SC).

According to some embodiments of the invention, the peptide is administered at a dose of 1.25 mg/kg.

According to some embodiments of the invention, the anti PD-1 is administered intravenously (IV).

According to some embodiments of the invention, the anti PD-1 is administered at a dose of 200 mg.

According to some embodiments of the invention, the chemotherapy is administered intravenously.

According to some embodiments of the invention, the treatment comprises a monotherapy period with the peptide followed by a combination therapy with the peptide, the anti PD-1 and the chemotherapy.

According to some embodiments of the invention, the combination therapy with the chemotherapy and the anti PD-1 is initiated on Day 8.

According to some embodiments of the invention, the combination therapy is repeated every 2 weeks with the chemotherapy and every 3 weeks with the anti PD-1.

According to some embodiments of the invention, the combination therapy with the peptide is initiated on Day 10 two times a week on non-consecutive days, 48 hours apart and at least 24 hours after the chemotherapy.

According to some embodiments of the invention, the monotherapy is and performed on Days 1-5, daily.

According to some embodiments of the invention, the treatment further comprises an anti-histamine and optionally analgesics.

According to some embodiments of the invention, the combination therapy continues for up to 35 treatments.

According to some embodiments of the invention, the subject is post first-line treatment against the metastatic pancreatic adenocarcinoma.

According to some embodiments of the invention, the first-line treatment comprises a gemcitabine-based chemotherapy.

According to some embodiments of the invention, the metastatic pancreatic adenocarcinoma is unresectable.

According to some embodiments of the invention, the metastatic pancreatic adenocarcinoma is pancreatic ductal adenocarcinoma.

According to some embodiments of the invention, the metastatic pancreatic ductal adenocarcinoma comprises intraductal papillary mucinous neoplasm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawing(s). With specific reference now to the drawing(s) in detail, it is stressed that the particulars shown are by way of example and for purposes of illustrative discussion of embodiments of the invention. In this regard, the description taken with the drawing(s) makes apparent to those skilled in the art how embodiments of the invention may be practiced.

In the drawing(s):

FIG. 1 is an illustration showing an embodiment of a treatment regimen.

DESCRIPTION OF SPECIFIC EMBODIMENTS OF THE INVENTION

The present invention, in some embodiments thereof, relates to methods and uses of agents for the treatment of pancreatic adenocarcinoma.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have developed, through laborious experimentation and screening a novel clinical protocol for the treatment of metastatic pancreatic adenocarcinoma in human subjects in need thereof.

Thus according to an aspect of the invention there is provided a method of treating metastatic pancreatic adenocarcinoma in a subject in need thereof, the method comprising administering to the subject a therapeutically effective amount of each of a peptide set forth in SEQ ID NO: 1, an anti PD-1 and a chemotherapy, thereby treating the metastatic pancreatic adenocarcinoma.

According to another aspect of the invention there is provided a therapeutically effective amount of each of a peptide set forth in SEQ ID NO: 1, an anti PD-1 and a chemotherapy for use in treating metastatic pancreatic adenocarcinoma in a subject in need thereof.

According to another aspect of the invention there is provided a therapeutically effective amount of each of a peptide set forth in SEQ ID NO: 1, an anti PD-1 and a chemotherapy for use in the treatment of metastatic pancreatic adenocarcinoma.

As used herein "metastatic pancreatic adenocarcinoma" refers to stage IIb to IV of the disease, when the tumor is present out of the pancreas i.e., lymph nodes or other distal locations.

TABLE 1

Stages of pancreatic cancer

| AJCC Stage | Stage grouping | Stage description* |
|---|---|---|
| 0 | Tis<br>N0<br>M0 | The cancer is confined to the top layers of pancreatic duct cells and has not invaded deeper tissues. It has not spread outside of the pancreas. These tumors are sometimes referred to as carcinoma in situ (Tis).<br>It has not spread to nearby lymph nodes (N0) or to distant sites (M0). |
| IA | T1<br>N0<br>M0 | The cancer is confined to the pancreas and is no bigger than 2 cm (0.8 inch) across (T1).<br>It has not spread to nearby lymph nodes (N0) or to distant sites (M0). |
| IB | T2<br>N0<br>M0 | The cancer is confined to the pancreas and is larger than 2 cm (0.8 inch) but no more than 4 cm (1.6 inches) across (T2).<br>It has not spread to nearby lymph nodes (N0) or to distant sites (M0). |
| IIA | T3<br>N0<br>M0 | The cancer is confined to the pancreas and is bigger than 4 cm (1.6 inches) across (T3).<br>It has not spread to nearby lymph nodes (N0) or to distant sites (M0). |
| IIB | T1<br>N1<br>M0 | The cancer is confined to the pancreas and is no bigger than 2 cm (0.8 inch) across (T1) AND it has spread to no more than 3 nearby lymph nodes (N1).<br>It has not spread to distant sites (M0). |
|  | T2<br>N1<br>M0 | The cancer is confined to the pancreas and is larger than 2 cm (0.8 inch) but no more than 4 cm (1.6 inches) across (T2) AND it has spread to no more than 3 nearby lymph nodes (N1).<br>It has not spread to distant sites (M0). |
|  | T3<br>N1<br>M0 | The cancer is confined to the pancreas and is bigger than 4 cm (1.6 inches) across (T3) AND it has spread to no more than 3 nearby lymph nodes (N1).<br>It has not spread to distant sites (M0). |
| III | T1<br>N2<br>M0 | The cancer is confined to the pancreas and is no bigger than 2 cm (0.8 inch) across (T1) AND it has spread to 4 or more nearby lymph nodes (N2).<br>It has not spread to distant sites (M0).<br>OR |
|  | T2<br>N2<br>M0 | The cancer is confined to the pancreas and is larger than 2 cm (0.8 inch) but no more than 4 cm (1.6 inches) across (T2) AND it has spread to 4 or more nearby lymph nodes (N2).<br>It has not spread to distant sites (M0).<br>OR |
|  | T3<br>N2<br>M0 | The cancer is confined to the pancreas and is bigger than 4 cm (1.6 inches) across (T3) AND it has spread to 4 or more nearby lymph nodes (N2).<br>It has not spread to distant sites (M0).<br>OR |
|  | T4<br>Any N<br>M0 | The cancer is growing outside the pancreas and into nearby major blood vessels (T4). The cancer may or may not have spread to nearby lymph nodes (Any N).<br>It has not spread to distant sites (M0). |
| IV | Any T<br>Any N<br>M1 | The cancer has spread to distant sites such as the liver, peritoneum (the lining of the abdominal cavity), lungs or bones (M1). It can be any size (Any T) and might or might not have spread to nearby lymph nodes (Any N). |

Adapted from - www(dot)cancer(dot)org/cancer/pancreatic-cancer/detection-diagnosis-staging/staging(dot)html According to a specific embodiment, the metastatic pancreatic adenocarcinoma is pancreatic ductal adenocarcinoma.

As used herein "pancreatic ductal adenocarcinoma" (PDAC) is a type of exocrine pancreatic cancer. It develops from cells lining small tubes in the pancreas called ducts (duct cells in the diagram above). These carry the digestive juices, which contain enzymes, into the main pancreatic duct and then on into the duodenum (first part of the small intestine). PDAC can grow anywhere in the pancreas, although it is most often found in the head of the pancreas.

According to a specific embodiment, the PDAC comprises intraductal papillary mucinous neoplasm.

In some embodiments, the pancreatic cancer is recurrent pancreatic cancer.

In some embodiments, the pancreatic cancer has reoccurred after remission.

In some embodiments, the individual has measurable disease (for example, according to RECIST criteria).

In some embodiments, the individual has one or more metastatic tumors measurable, for example, by CT scan (or MRI).

In some embodiments, the pancreatic cancer is unresectable pancreatic cancer. In some embodiments, the pancreatic cancer is a resectable pancreatic cancer.

In some embodiments, the pancreatic cancer is borderline resectable.

In some embodiments, the primary location of the pancreatic cancer is the head of the pancreas. In some embodiments, the primary location of the pancreatic cancer is the body of the pancreas. In some embodiments, the primary location of the pancreatic cancer is the tail of the pancreas.

As used herein "subject" refers to a human subject diagnosed with metastatic pancreatic adenocarcinoma.

In some embodiments, the subject is a female. In some embodiments, the individual is a male. In some embodiments, the individual is under about 65 years old (such as under about any of 60, 55, 50, 45, or 40 years old). In some embodiments, the subject is at least about 65 years old (such as at least about any of 70, 75, or 80 years old).

According to a specific embodiment, the subject is at least 18 years

According to a specific embodiment, the treatment is post first-line treatment against the pancreatic adenocarcinoma.

Thus, methods, articles and compositions described herein may also be used as a second line or third line therapy after the prior treatment for pancreatic cancer has failed or has substantially failed, or the pancreatic cancer is substantially refractory to the first line therapy. In some embodiments, the individual has received at least one line of therapy (e.g., chemotherapy or immunotherapy) for treating pancreatic cancer (e.g., metastatic pancreatic cancer) prior to receiving the treatment described herein. In some embodiments, the patient has received 1 line of therapy or 2 lines of therapy (e.g., 1 line of chemotherapy or immunotherapy). Thus, the treatment described herein may be used as a second line therapy. The prior line of therapy described herein may be a prior line of chemotherapy or immunotherapy. The first line of therapy may comprise any of the following: gemcitabine, 5-FU, masitinib, paclitaxel, trametinib and/or erlotinib.

According to a specific embodiment, the first line treatment is gemcitabine-based chemotherapy e.g., under the brand name Gemzar™, among others.

According to a specific embodiment, the disease showed radiographic progression after stopping treatment with first-line, e.g., gemcitabine-based, chemotherapy.

As used herein, the term "treating" includes abrogating, substantially inhibiting, slowing or reversing the progression of a condition, substantially ameliorating clinical symptoms of the metastatic pancreatic adenocarcinoma.

According to a specific embodiment, the subject is diagnosed with metastatic pancreatic adenocarcinoma.

According to a specific embodiment the metastatic pancreatic adenocarcinoma is histologically confirmed (either previously or newly biopsied).

According to a specific embodiment, the subject has a measurable disease (≥1 measurable lesion) based on Response Evaluation Criteria In Solid Tumors (RECIST) v1.1.

According to a specific embodiment, tumor lesions situated in a previously irradiated area are considered measurable if progression has been demonstrated in such lesions.

According to a specific embodiment, the subject has histologically confirmed (either previously or newly biopsied) metastatic unresectable pancreatic adenocarcinoma, including with intraductal papillary mucinous neoplasm.

According to a specific embodiment the pancreatic cancer is not acinar cell carcinoma, pancreaticoblastoma, malignant cystic neoplasms, endocrine neoplasms, squamous cell carcinoma. Vater and periampullary duodenal or common bile duct malignancies.

According to a specific embodiment the subject does not have a bowel obstruction According to a specific embodiment, the subject is not immune-deficient.

According to a specific embodiment, the subject does not have an active autoimmune disease that has required systemic treatment in the 2 years preceding the treatment (i.e., with the use of disease-modifying agents, corticosteroids or immunosuppressive drugs).

According to a specific embodiment, the subject does not have a history of (non-infectious) pneumonitis that required steroids or current pneumonitis.

According to a specific embodiment, the subject does not have a history of interstitial lung disease.

As used herein "a peptide set forth in SEQ ID NO: 1" also referred to as BL-8040 (previously named "BKT140") is a highly selective CXCR4 antagonist, a novel therapy for the treatment of cancer. The peptide is a 14-residue, cyclic, synthetic peptide capped with an aromatic ring that binds to CXCR4 with high affinity ($IC_{50}$ 0.54-4.5 nM) and inhibits its function [Tamamura H, Hiramatsu K, Kusano S, Terakubo S, Yamamoto N, Trent J O, et al. Synthesis of potent CXCR4 inhibitors possessing low cytotoxicity and improved biostability based on T140 derivatives. Org Biomol Chem 2003; 1:3656-3662].

According to a specific embodiment, the BL-8040 is manufactured as a white to off-white powder synthetic polypeptide, freely soluble in water and in 0.45% Sodium Chloride (half normal saline). It is manufactured in accordance with current Good Manufacturing Practice (cGMP) by BioConnection B.V. (previously MSD), Kloosterstraat 9, 5349 AB Oss, Netherlands.

PD1 (Programmed Death 1, also known as CD279) is a 55 kDa type I transmembrane protein that is part of the Ig gene superfamily, which is expressed on the surface of several immune cells such as activated T cells, B cells, NK cells and myeloid cells. PD-1 contains a membrane proximal immunoreceptor tyrosine inhibitory motif (ITIM) and a membrane distal tyrosine-based switch motif (ITSM).

The presence of an ITIM on PD-1 indicates that this molecule functions to attenuate antigen receptor signaling by recruitment of cytoplasmic phosphatases.

According to a specific embodiment, the PD1 protein refers to the human protein, such as provided in the following GenBank Number NP_005009. Two ligands for PD-1 have been identified, PD-L1 and PD-L2 (also known as B7-DC).

PD1 pattern of expression and function is dependent on the cell type. PD1 expression is induced following effector T cells activation. Upon ligand binding, PD1 inhibits kinases that are involved in T cell activation through e.g. the phosphatase SHP2, thereby transmits an inhibitory signal. Conversely, PD1 is highly expressed on regulatory T cells, where it may enhance their proliferation upon ligand binding. PD-1 is also induced on other activated non-T lymphocyte subsets, including B cells and NK cells, where upon ligand binding it transmits an inhibitory signal which limits their antibody production and lytic activity, respectively [Pardon (2012) Nature Reviews Cancer 12, 252-264].

As used herein "anti PD-1" refers to an antibody which binds PD-1 and prevents and/or inhibits the biological function of PD1.

According to specific embodiments, the PD1 antagonist prevents and/or inhibits signaling to an immune cell (e.g. T cells, B cells, NK cells) by PD1; thereby suppresses PD1 immune-suppressive activity.

The term "antibody" as used in this invention includes intact molecules as well as functional fragments thereof (that are capable of binding to an epitope of an antigen).

As used herein, the term "epitope" refers to any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

According to a specific embodiment, the antibody fragments include, but are not limited to, single chain, Fab, Fab' and F(ab')2 fragments, Fd, Fcab, Fv, dsFv, scFvs, diabodies, minibodies, nanobodies, Fab expression library or single domain molecules such as VH and VL that are capable of binding to an epitope of the antigen in an HLA restricted manner.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv Fv (scFv), a disulfide-stabilized Fv (dsFv), an Fab, an Fab', and an F(ab')2, or antibody fragments comprising the Fc region of an antibody.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989.), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008).

As used herein, the "variable regions" and "CDRs" may refer to variable regions and CDRs defined by any approach known in the art, including combinations of approaches.

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds);

(vii) Single domain antibodies or nanobodies are composed of a single VH or VL domains which exhibit sufficient affinity to the antigen; and (viii) Fcab, a fragment of an antibody molecule containing the Fc portion of an antibody developed as an antigen-binding domain by introducing antigen-binding ability into the Fc region of the antibody.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Exemplary methods for generating antibodies employ induction of in-vivo production of antibody molecules, screening of immunoglobulin libraries (Orlandi D. R. et al., 1989. Proc. Natl. Acad. Sci. U.S.A. 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256:495-497; Kozbor D. et al., 1985. J. Immunol. Methods 81:31-42; Cote R J. et al., 1983. Proc.

Natl. Acad. Sci. U.S.A. 80:2026-2030; Cole S P. et al., 1984. Mol. Cell. Biol. 62:109-120).

In cases where target antigens are too small to elicit an adequate immunogenic response when generating antibodies in-vivo, such antigens (haptens) can be coupled to antigenically neutral carriers such as keyhole limpet hemocyanin (KLH) or serum albumin [e.g., bovine serum albumine (BSA)] carriers (see, for example, U.S. Pat. Nos. 5,189,178 and 5,239,078]. Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

As described hereinabove, Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

As mentioned, the antibody fragment may comprise a Fc region of an antibody termed "Fcab". Such antibody fragments typically comprise the CH2-CH3 domains of an antibody. Fcabs are engineering to comprise at least one modification in a structural loop region of the antibody, i.e. in a CH3 region of the heavy chain. Such antibody fragments can be generated, for example, as follows: providing a nucleic acid encoding an antibody comprising at least one structural loop region (e.g. Fc region), modifying at least one nucleotide residue of the at least one structural loop regions, transferring the modified nucleic acid in an expression system, expressing the modified antibody, contacting the expressed modified antibody with an epitope, and determining whether the modified antibody binds to the epitope. See, for example, U.S. Pat. Nos. 9,045,528 and 9,133,274 incorporated herein by reference in their entirety.

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Anti-PD1 antibodies suitable for use in the invention can be generated using methods well known in the art especially in light of the detailed description hereinabove. Alternatively, art recognized anti-PD1 antibodies can be used. Examples of anti-PD1 antibodies are disclosed for example in Topalian, et al. NEJM 2012, U.S. Pat. Nos. 7,488,802; 8,008,449; 8,609,089; 6,808,710; 7,521,051; and 8,168,757, U.S. Patent Application Publication Nos. 20140227262; 20100151492; 20060210567; and 20060034826 and International Patent Application Publication Nos. WO2008156712; WO2010089411; WO2010036959; WO2011159877; WO2013/019906; WO2014159562; WO2011109789; WO01/14557; WO2004/004771; and WO2004/056875, which are hereby incorporated by reference in their entirety.

Specific anti-PD1 antibodies that can be used according to some embodiments of the present invention include, but are not limited to:

Nivolumab (also known as MDX1106, BMS-936558, ONO-4538), marketed by BMY as Opdivo, a fully human IgG4 antibody with the structure described in WHO Drug Information, Vol. 27, No. 1, pages 68-69 (2013) that binds to and blocks the activation of PD-1 by its ligands PD-L1 and PD-L2;

Pidilizumab (also known as CT-011, hBAT, hBAT-1, produced by CureTech), a humanized monoclonal IgG1 antibody that binds PD-1;

AMP-514 (also known as MEDI-0680, produced by AZY and MedImmune), a humanized monoclonal IgG4 antibody that binds PD-1.

Humanized antibodies h409A1 1, h409A16 and h409A17, which are described in PCT Patent Application No. WO2008/156712;

According to a specific embodiment, the anti PD-1 is Pembrolizumab (also known as MK-3475, Keytruda, SCH 900475, produced by Merck). A humanized monoclonal IgG4 antibody with the structure described in WHO Drug Information, Vol. 27, No. 2, pages 161-162 (2013) that binds to and blocks the activation of PD1 by its ligands;

As mentioned, the present teachings contemplate the use of chemotherapy for the treatment of the disease. Examples include but are not limited to, gemtabicine, FOLFIRINOX, erlotinib, 5-fluorouracil, paclitaxel, nab-paclitaxel, docetaxel, capecitabine, oxaliplatin cisplatin, FOLFOXIRI, abraxane, an anti-CD40 antibody, oregovomab, Nelfinavir, cetuximab, tegafur, leucovorin, irinotecan and combinations thereof.

According to a specific embodiment the chemotherapy is irinotecan, a topoisomerase inhibitor.

Irinotecan is converted by esterase enzymes into the more active metabolite, SN-38. The chemical name of irinotecan is (S)-4,11-diethyl-3,4,12,14-tetrahydro-4-hydroxy-3,14-dioxo1H-pyrano [4',4'-:6,7]-indolizino [1,2-b]quinolin-9-yl-[1,4'bipiperidine]-1'-carboxylate. Irinotecan hydrochloride trihydrate is also referred to by the name CPT-11 and by the trade name CAMPTOSAR®.

The topoisomerase inhibitor can be camptothecin conjugated to a biocompatible polymer such as a cyclodextrin or cyclodextrin analog (e.g., sulfonated cyclodextrins). For example, the topoisomerase inhibitor can be a cyclodextrin-containing polymer chemically bound to a camptothecin, irinotecan, SN-38 or other topoisomerase 1 inhibitor compound. A cyclodextrin-camptothecin conjugated topoisomerase 1 inhibitor can be administered at a pharmaceutically acceptable dose including 6, 12, or 18 mg/m2 weekly administration, or 12, 15 or 18 mg/m2 biweekly administration. Examples of camptothecin-cyclodextrin conjugate topoisomerase 1 inhibitors (e.g., the cyclodextrin-containing polymer conjugate with camptothecin designated "CRLX101"), and related intermediates for preparing the same, are disclosed, for example, in Greenwald et al., Bioorg. Med. Chem., 1998, 6, 551-562, as well as United States Patent Application 2010/0247668, United States Patent Application 2011/0160159 and United States Patent Application 2011/0189092.

The topoisomerase inhibitor can also be a liposomal formulation of a topoisomerase inhibitor such as irinotecan, camptothecin or topotecan. Liposomal irinotecan (e.g., MM-398, also called "nal-IRI") is a highly stabilized liposomal formulation of irinotecan that provides for sustained exposure of irinotecan, and the active metabolite SN-38 in the tumor to a higher proportion of cells during the more sensitive S-phase of the cell cycle. MM-398 is a liposomal irinotecan that has shown promising preclinical and clinical activity in a range of cancer types, and was recently approved in the United States in combination with 5-FU/LV for patients with metastatic adenocarcinoma of the pancreas after disease progression following gemcitabine-based therapy. Compared with free irinotecan, nal-IRI has an extended PK profile with prolonged local tumor exposure of MM-398 and SN-38. Since SN-38 is cleared more quickly from normal tissues than from tumor, it is hypothesized that delayed dosing of veliparib relative to MM-398 will allow for the expected window of maximum irinotecan-induced toxicity to pass in the absence of concurrent veliparib toxicity. However, the tumor levels of SN-38 are predicted to be sustained upon subsequent veliparib dosing, therefore maintaining the ability of both drugs to act on tumor tissue simultaneously and maintain synergy.

One suitable liposomal Top1 inhibitor formulation is liposomal irinotecan available under the brand name ONIVYDE®. (irinotecan liposome injection) (Merrimack Pharmaceuticals, Inc. Cambridge, Mass.), previously designated "MM-398" prior to FDA approval, and liposomal irinotecan products that are bioequivalent to ONIVYDE. The ONIVYDE/MM-398 (irinotecan liposome injection) includes irinotecan as an irinotecan sucrosofate salt encapsulated in liposomes for intravenous use. The drug product liposome is a small unilamellar lipid bilayer vesicle, approximately 110 nm in diameter, which encapsulates an aqueous space which contains irinotecan in a gelated or precipitated state, as the sucrosofate salt. The liposome carriers are composed of 1,2-distearoyl-sn-glycero-3-phosphocholine (DSPC), 6.81 mg/mL; cholesterol, 2.22 mg/mL; and methoxy-terminated polyethylene glycol (MW 2000)-distearoylphosphatidylethanolamine (MPEG-2000-DSPE), 0.12 mg/mL. Each mL also contains 2-[4-(2-hydroxyethyl) piperazin-1-yl]ethanesulfonic acid (HEPES) as a buffer, 4.05 mg/mL; sodium chloride as isotonicity reagent, 8.42 mg/mL, ONIVYDE/MM-398 is believed to include about 80,000 molecules of irinotecan in a gelated or precipitated state as a sucrosofate salt, encapsulated in a liposome of about 100 nm in diameter.

Gemcitabine (e.g., Gemzar™) or Gemcitabine-based chemotherapy e.g., combined with other drugs such as albumin-bound paclitaxel (Abraxane), erlotinib (Tarceva), or capecitabine (Xeloda) or combined with radiation (this is called chemoradiation).

As used herein "leucovorin" refers to folinic acid that is typically administered in combination with Onivyde® and 5-FU.

5-FU is a thymidylate synthase (TS) inhibitor. Interrupting the action of this enzyme blocks synthesis of the pyrimidine thymidine, which is a nucleoside required for DNA replication. Thymidylate synthase methylates deoxyuridine monophosphate (dUMP) to form thymidine monophosphate (dTMP). Administration of 5-FU causes a scarcity in dTMP, so rapidly dividing cancerous cells undergo cell death via thymineless death. Calcium folinate provides an exogenous source of reduced folinates and hence stabilises the 5-FU-TS complex, hence enhancing 5-FU's cytotoxicity. 5-FU is sold under the brand name Adrucil, among others.

According to a specific embodiment, the chemotherapy comprises a plurality of chemotherapeutic agents e.g., at least 2, or at least 3, e.g., 2, 3, 4, 5 chemotherapeutic agents).

According to a specific embodiment, the chemotherapy comprises irinotecan (e.g., liposome-encapsulated e.g., Onivyde®), 5-FU and Leucovorin.

According to a specific embodiment treatment does not include oxaliplatin.

The peptide, antibody and chemotherapy ("agents") described hereinabove can be administered to the subject per se, or in a pharmaceutical composition where it is mixed with suitable carriers or excipients. Each of the agents can be formulated in a separate formulation or at least some of them combined to a single formulation.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agents accountable for the biological effect, e.g., SEQ ID NO: 1, Pembrolizumab, Irinotecan (e.g., liposome-encapsulated e.g., Onivyde®), 5-FU and Leucovorin.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, intradermal, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

According to a specific embodiment, the peptide of the invention or the pharmaceutical composition comprising same is administered subcutaneously.

According to a specific embodiment, the anti PD-1 antibody (e.g., Pembrolizumab) or the pharmaceutical composition comprising same is administered intravenously.

According to a specific embodiment, the chemotherapy or the pharmaceutical composition comprising same is administered intravenously.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

Pharmaceutical compositions suitable for use in context of some embodiments of the invention include compositions wherein the active ingredients are contained in an amount effective to achieve the intended purpose. More specifically, according to specific embodiments, a therapeutically effective amount means an amount of active ingredients effective to prevent, alleviate or ameliorate symptoms of a disorder (i.e., metastatic pancreatic adenocarcinoma) or prolong the survival of the subject being treated.

According to specific embodiments the peptide of the invention or the pharmaceutical composition comprising same is administered in a dose ranging between 0.1 to 10 mg/kg of body weight, between 0.1 to 2 mg/kg of body weight, between 0.1 to 1 mg/kg of body weight, between 0.3 to 10 mg/kg of body weight, between 0.3 to 2.

According to a specific embodiment, BL-8040 is administered at a dose of 1-2 mg/kg body weight.

According to a specific embodiment, the, BL-8040 is administered at a dose of 1.25-1.5 mg/kg body weight.

According to a specific embodiment, the BL-8040 is administered at a dose of 1.25 mg/kg body weight.

According to a specific embodiment, the BL-8040 is administered subcutaneously (SC).

According to a specific embodiment, the anti PD-1 e.g., Pembrolizumab is administered at a dose ranging between 0.001 to 30 mg/kg body weight, between 0.001 to 20 mg/kg body weight, between 0.001 to 10 mg/kg body weight, between 0.001 to 1 mg/kg body weight, between 0.01 to 30 mg/kg body weight, between 0.01 to 20 mg/kg body weight, between 0.01 to 10 mg/kg body weight, between 0.01 to 1 mg/kg body weight, between 0.1 to 30 mg/kg body weight, between 0.1 to 20 mg/kg body weight, between 0.1 to 10 mg/kg body weight, between 0.1 to 5 mg/kg body weight, between 1 to about 30 mg/kg, between 1 to about 20 mg/kg or between 2 to about 10 mg/kg, between 0.5 to about 30 mg/kg, between 0.5 to about 20 mg/kg, 0.5 to about 20 mg/kg, 1 to about 5 mg/kg, 1 to about 5 mg/kg.

According to a specific embodiment the anti PD-1 e.g., Pembrolizumab, is administered at a dose of 2.85 mg/kg.

According to a specific embodiment, the anti PD-1 e.g., Pembrolizumab, is administered at a dose of 1-500 mg, 1-400 mg, 1-300 mg, 1-200 mg, 10-500 mg, 50-500 mg, 100-500 mg, 100-300 mg or 150-450 mg.

According to a specific embodiment, the anti PD-1 (e.g., Pembrolizumab) is administered intravenously (IV).

According to a specific embodiment, the anti PD-1 is administered at a fixed dose of 200 mg.

According to a specific embodiment, the chemotherapy is administered intravenously.

According to a specific embodiment, the chemotherapy is administered according to the tolerated dose which is known in the field.

According to a specific embodiment, the doses are Onivyde® 70 mg/m$^2$, leucovorin 400 mg/m$^2$ and fluorouracil 2400 mg/m$^2$.

The regimen of administration can be as follows:

IV Onivyde® over 90 minutes, followed by IV leucovorin 400 mg/m$^2$ over 30 minutes, followed by IV fluorouracil 2400 mg/m$^2$ over 46 hours, once every two weeks.

According to a specific embodiment, the treatment comprises a monotherapy period with said peptide followed by a combination therapy with said peptide, said anti PD-1 and said chemotherapy.

As used herein "monotherapy" refers to a use of a single drug to treat the cancer. The term does not exclude using other medications for treating symptoms that are not associated with the disease per se. For instance the use of analgesics and/or anti-histamine, and/or anti-nausea medications is still contemplated during the period of monotherapy. The term excludes the use of anti-cancer drugs (which are defined as such) during the time of monotherapy.

According to a specific embodiment, the time period of monotherapy is up to 7 days.

According to a specific embodiment, the time period of monotherapy is 5 days (e.g., daily).

As used herein "combination therapy" refers to the use of a plurality of anti-cancer drugs (peptide, chemotherapy, anti PD-1) such as in an embodiment of the invention.

According to a specific embodiment, the combination therapy with said chemotherapy and said anti PD-1 is initiated on Day 6-10.

According to a specific embodiment, the combination therapy with said chemotherapy and said anti PD-1 is initiated on Day 8.

According to a specific embodiment, the combination therapy is repeated every 2 weeks with said chemotherapy and every 3 weeks with said anti PD-1.

According to a specific embodiment, the peptide is administered at the monotherapy period, followed by administration of the antibody and chemotherapy.

According to a specific embodiment the combination therapy with the peptide is initiated on Day 10 two times a week on non-consecutive days, 48 hours apart (optionally at least 24 hours after said chemotherapy).

According to a specific embodiment the monotherapy is and performed on Days 1-5, daily.

Without being bound by theory, it is suggested that cytotoxic chemotherapy induces tumor death and reduces tumor burden. The cytotoxic chemotherapy may induce immunogenic cell death leading to activation and expansion of new tumor-reactive T cell clones. BL-8040 facilitates the infiltration of these T cells into the tumor core. BL-8040 reduces the T-reg and (myeloid derived suppressor cells) MDSC and therefore reduces the immunosuppressive microenvironment. Pembrolizumab maintains/restores the activity of the T cells within the tumor.

Following are specific embodiments of the invention, thus:

Pembrolizumab (MK-3475) Solution for Infusion is a sterile, non-pyrogenic aqueous solution supplied in single-use Type I glass vial containing 100 mg/4 mL of pembrolizumab (MK-3475). The product is preservative-free solution which is essentially free of extraneous particulates.

Chemotherapy: Onivyde®/5-FU/LV

Onivyde is an injection: 43 mg/10 mL irinotecan free base as a white to slightly yellow, opaque, liposomal dispersion in a single-dose vial.

Fluorouracil injection is supplied as a pharmacy bulk package as a vial containing 2.5 g/50 mL (50 mg/mL) fluorouracil.

Leucovorin Calcium for injection is supplied as a sterile lyophilized powder. The 350 mg vial is preservative-free. The inactive ingredient is sodium chloride 140 mg/vial for the 350 mg vial. Sodium hydroxide and/or hydrochloric acid are used to adjust the pH to approximately 8.1 during manufacture. 1 mg of leucovorin calcium contains 0.002 mmol of leucovorin and 0.002 mmol of calcium.

BL-8040 is administrated by SC injection of 1.25 mg/kg daily as monotherapy for 5 days, beginning on Day 1 daily through Day 5. Subjects receive once daily SC injections of BL-8040 in the morning. Pre-medication with systemic antihistamines with or without analgesics can be administered in order to minimize the occurrence of BL-8040 related local injection site reactions and/or systemic reactions.

According to a specific embodiment, the BL-8040 injection site is rotated to minimize the severity of any local injection site reactions. If the dose volume after reconstitution is higher than 2 ml, injections are split in order to have less than 2 ml per injection; at the discretion of the treating professional, a single-dose administration may be split and injected into more than one site. According to a specific embodiment, the same instructions are applicable for combination period of the treatment.

It will be appreciated that according to a specific embodiment, BL-8040 injections are skipped in case of a significant increase in WBC (e.g., WBC>60,000/µL) measured prior to administration of the next BL-8040 injection and/or evidence of leukostasis. BL-8040 treatment is resumed provided there are no signs of leukostasis and or the WBC decrease to values ≤60,000/µL.

After monotherapy, BL-8040 is administered as part of the combination treatment with pembrolizumab in cycles of three-week duration and chemo in cycles of two-weeks. According to a specific embodiment, the dosing is as follows:

During the combination period, BL-8040 is administered two times a week on non-consecutive days, 48 hours apart and at least 24 hours after chemotherapy, as a SC injection during the morning.

Treatment with pembrolizumab begins following the monotherapy period and as a part of the combination therapy. During the combination period pembrolizumab is administered at a dose of 200 mg using a 30-minute IV infusion on Day 1 of each 3-week treatment. According to a specific embodiment, pembrolizumab may be administered up to 3 days before or after the scheduled Day 1 of each cycle due to administrative reasons.

According to a specific embodiment, Pembrolizumab is administered as a dose of 200 mg using a 30-minute IV infusion. Given the variability of infusion pumps, a window between −5 minutes and +10 minutes is allowed (i.e., infusion time is 30 minutes−5 min/+10 min).

It will be appreciated and according to a specific embodiment, when pembrolizumab is provided on the same day of BL-8040, BL-8040 administration 1 hour (±0.5 hour) after the end of the pembrolizumab infusion.

It will be appreciated and according to a specific embodiment, when pembrolizumab is provided in the same day of the chemotherapy, pembrolizumab should be administered first, followed by the chemotherapy.

According to a specific embodiment, the Onivyde is administered prior to LV and 5-FU. Onivyde 70 mg/m$^2$ as an IV infusion over 90 minutes, followed by LV 400 mg/m$^2$ IV over 30 minutes, followed by 5-FU 2400 mg/m$^2$ IV over 46 hours, every 2 weeks. Patients homozygous for the UGT1A1*28 allele will initiate Onivyde® at 50 mg/m$^2$, and the dose can be increased if tolerated at later (e.g., 35 cycles).

FIG. 1 shows a specific treatment regimen according to an embodiment of the invention.

Efficacy testing can be done at any time of the execution of the regimen as described herein e.g., following at least 1, 2, 3, 5, 10 or more cycles of the therapy (e.g., as disclosed in FIG. 1). To clarify, a cycle refers to the combination treatment, e.g., according to the pembrolizumab three-week-cycle schedule of treatment.

Efficacy Testing
Imaging Assessment

Imagining is used for assessment of response. For example, CT or MRI may be used. The same imaging method should be used throughout the treatment for each subject.

According to a specific embodiment, the imaging assessment can be done at:
Time for subject selection to the treatment.
End of Monotherapy period, Day 5.
Combination treatment at the end of Cycle 2 and then every 3 cycles up to one year of treatment (Cycle 17) and then every 4 cycles until end of treatment.

According to a specific embodiment, RECIST 1.1 is adapted to account for the unique tumor response characteristics seen with treatment of immunotherapeutic agents. Agents such as pembrolizumab and BL-8040 may produce antitumor effects by potentiating endogenous cancer-specific immune responses. The response patterns seen with such an approach may extend beyond the typical time course of responses seen with cytotoxic agents and can manifest a clinical response after an initial increase in tumor burden or even the appearance of new lesions:

If radiologic imaging verifies initial progressive disease, tumor assessment should be repeated ≥4 weeks later in order to confirm progressive disease with the option of continuing treatment per below.

If repeat imaging shows less than a 20% increase in tumor burden compared to nadir, stable or improved previous new lesion (if identified as cause for initial progressive disease), and stable/improved non-target lesions (if identified as cause for initial progressive disease), treatment may be continued/resumed.

If repeat imaging confirms progressive disease due to any of the scenarios list below, subjects are discontinued from therapy.

In determining whether or not the tumor burden has increased or decreased, all target lesions as well as non-target lesions are considered.

Scenarios where progressive disease is confirmed at repeat imaging:
Tumor burden remains increased by ≥20% and at least 5 mm absolute increase compared to nadir
Non-target lesions resulting in initial progressive disease is worse (qualitative)
New lesion resulting in initial progressive disease is worse (qualitative)
Additional new lesion(s) since last evaluation.

In subjects who have initial evidence of radiological progressive disease, it is at the discretion of the treating physician whether to continue a subject on treatment until repeat imaging is obtained. This clinical judgment decision should be based on the subject's overall clinical condition, including performance status, clinical symptoms, and laboratory data. Subjects may continue to receive treatment while waiting for confirmation of progressive disease if they are clinically stable as defined by the following criteria:
Absence of signs and symptoms indicating disease progression
No decline in ECOG performance status
Absence of rapid progression of disease
Absence of progressive tumor at critical anatomical sites (e.g., cord compression) requiring urgent alternative medical intervention.

When feasible, subjects should not be discontinued until progression is confirmed. This allowance to continue treatment despite initial radiologic progression takes into account the observation that some subjects can have a transient tumor flare in the first few months after the start of immunotherapy, but with subsequent disease response. Subjects that are deemed clinically unstable are not required to have repeat imaging for confirmation of progressive disease.

If the physician assesses disease progression and the subject is clinically stable (described above), it is at the discretion of the physician to continue to treat and image the subject at least 4 weeks after the first tumor imaging indicating progressive disease. irRECIST would then be followed by the physician to determine if the follow-up tumor imaging confirms progressive disease. Subjects who have unconfirmed disease progression may continue on treatment and follow the regular imaging schedule intervals until progression is confirmed, provided they have met the conditions detailed above.

irRECIST Assessment of Disease

As noted above, if tumor imaging shows initial disease progression, the study site may elect to continue treatment, repeat imaging ≥4 weeks later and assess tumor response or confirmed progression per irRECIST.

Biopsy Analysis

According to a specific embodiment, biopsy can be performed at Screening and will be assessed for: tumor mutation burden (TMB), PD-L1 and DNA mismatch repair status.

Blood Sampling and Processing

Samples are collected for safety and efficacy analysis, e.g., CBC, anti-drug antibodies titer and determination of BL-8040 plasma concentrations.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Objectives

The objectives of the study are to assess the efficacy and safety of BL8040/Pembrolizumab in combination with liposomal irinotecan (Onivyde®)/5-fluorouracil/leucovorin (5-FU/LV) in subjects with metastatic pancreatic adenocarcinoma. The mechanism of action of BL-8040, alone and when given in combination, is studied further using blood and tumor tissue samples.

Study Endpoints

Primary Endpoint

Objective Response Rate ($ORR_{RECIST1.1}$) determined according to Response Evaluation Criteria In Solid Tumors (RECIST) v1.1 criteria.

Secondary Endpoint

Objective Response Rate ($ORR_{irRECIST}$) determined according to irRECIST criteria.

OS.

PFS.

Disease Control according to RECIST 1.1 ($DC_{RECIST1.1}$) is defined as the sum of partial responses (PRs), CRs and SDs.

Safety and Tolerability

TEAEs

Laboratory safety data

Vital signs

ECG

Physical examination (PE)

Early study discontinuations, overall and due to AE

Exploratory
  Change in tumor marker (CA19-9) from Baseline.
  Further tumor tissue analysis.

Example 2

Study Design

This is an open-label, single arm, Phase IIa study in subjects with metastatic pancreatic adenocarcinoma. The study consists of two periods:
  Monotherapy period: One week, with treatment using BL-8040 on Days 1-5
  Combination therapy:
  Onivyde®/5-FU/LV every 2 weeks, pembrolizumab once every 3 weeks and BL-8040 twice a week.

Subjects with metastatic pancreatic adenocarcinoma that has progressed following first-line treatment with gemcitabine-based chemotherapy are enrolled and receive BL-8040 monotherapy for five days followed by a combination treatment of BL-8040, pembrolizumab and chemotherapy. During the monotherapy period, eligible subjects receive daily SC injections of BL-8040 (1.25 mg/kg) on Days 1-5.

From Day 8, subjects will begin a combination period consisting of:
  IV Onivyde® 70 mg/m² over 90 minutes followed by IV leucovorin (LV) 400 mg/m² over 30 minutes, followed by IV fluorouracil (5-FU) 2400 mg/m² over 46 hours, every 2 weeks.
  Pembrolizumab 200 mg once every three weeks.
  Beginning on Day 10, BL-8040 twice a week and at least 24 hours after chemotherapy dosing.

The combination therapy continues for up to 35 treatments (approximately two years), or until progression, clinical deterioration or early termination, whichever comes first.

An independent data monitoring committee (DMC) reviews the accumulated study data according to the DMC charter in order to ensure subject welfare. Serious AEs (SAEs) are monitored continuously throughout the study.

Safety review of the accumulated data of subjects is performed by the independent DMC when the first 6 subjects and potentially when staggered to 12 subjects (Safety Dose-Limiting Toxicity (DLT) Cohort) have completed 28 days of treatment including monotherapy and combination treatment. The guidelines to be used by the DMC for the review of the Safety DLT Cohort are presented below:
  If 0 out of 6 subjects experience a DLT during the first cycle of treatment, the combination treatment will be considered as eligible for further evaluation and recruitment will continue without a pause.
  If 1 out of 6 subjects experiences a DLT, the Safety DLT Cohort will be expanded to 12 subjects.
  If ≥2 out of 6 subjects experience a DLT, the DMC will assess the risk/benefit ratio of the combination treatment and recommend one or more of the following: 1) the Safety DLT Cohort should be expanded to 12 subjects, 2) the protocol should be modified, 3) the treatment schedule should be changed or 4) the study should be discontinued.
  If ≤2 out of 12 subjects experience a DLT in the expanded Safety DLT Cohort, recruitment can be continued to the full proposed study size.
  If >2 out of 12 subjects experience a DLT in the expanded Safety DLT Cohort, the DMC will determine whether recruitment will be stopped, or recruitment can be continued with or without a protocol modification.

Efficacy data will be assessed throughout the study, without stopping recruitment. The assessment will include review all the available data, i.e. imaging, biopsies, safety assessment, etc. and will assess the clinical benefit of the investigated combination treatments.

Example 3

Study Population

Male and female subjects 18 years old and older with metastatic unresectable PDAC are enrolled in this trial. Inclusion/Exclusion criteria are assessed during the Screening period unless otherwise specified within the specific criteria.

Entry criteria are absolute. Any subject not meeting one or more inclusion criteria or meeting one or more Exclusion Criteria is not allowed to enter the trial. If a variable's limit is presented in a criterion, then that limit may not be exceeded.

Inclusion Criteria

In order to be eligible for participation in this trial, the subject must satisfy the following:
  1. 18 years and older
  2. Patients must sign a written informed consent prior to entering the study.
  3. Histologically confirmed (either previously or newly biopsied) metastatic unresectable pancreatic adenocarcinoma, including intraductal papillary mucinous neoplasm.
  4. Have measurable disease (≥1 measurable lesion) based on RECIST v1.1 as determined by the site team. Tumor lesions situated in a previously irradiated area are considered measurable if progression has been demonstrated in such lesions.
  5. Previous treatment lines
  Have documented objective radiographic progression after stopping treatment with first-line, gemcitabine-based chemotherapy. Only primary metastatic patients are allowed to participate. Patients with previous surgery for their pancreatic cancer will not be allowed to participate.
  6. Willing to submit an evaluable tumor tissue sample, preferably from a liver metastasis, unless tumor is considered inaccessible or biopsy is otherwise considered not in the subject's best interest.
  7. Complete resolution of toxic effect(s) of the most recent prior chemotherapy to Grade 1 or less (except alopecia). If the subject received major surgery or radiation therapy of >30 Gy, they must have recovered from the toxicity and/or complications from the intervention.
  8. ECOG status ≤1.
  9. Life expectancy of at least 3 months.
  10. Adequate organ function at Baseline as defined below.
All laboratory assessments should be performed within 10 days of treatment initiation
a. Hematological:
  White blood cell (WBC)≥2,500/mm^3
  Absolute neutrophil count ≥1500/mm^3
  Platelet count ≥100,000/mm^3
  Hemoglobin ≥9 g/dL or ≥5.6 mmol/L
  Hematocrit ≥30%
b. Renal Function:
  Creatinine ≤1.5× Upper limit of normal (ULN) OR measured or calculated creatinine clearance (glomerular filtration rate [GFR]) can also be used in place of creatinine or (CrCl)≥60 mL/min for subject with creatinine levels >1.5× institutional ULN c. Hepatic Function:
   Total Bilirubin: within institutional normal ranges
   Aspartate aminotransferase/serum glutamic oxaloacetic transaminase (AST/SGOT) and Alanine amino transferase/serum glutamate-pyruvate transaminase (ALT/SGPT): ≤2.5×ULN OR ≤5×ULN for subjects with liver metastases
d. Coagulation:
   INR or PT: ≤1.5×ULN unless subject is receiving anticoagulant therapy as long as PT or PTT is within therapeutic range of intended use of anticoagulants
   aPTT: ≤1.5×ULN unless subject is receiving anticoagulant therapy as long as PT or PTT is within therapeutic range of intended use of anticoagulants
11. Subjects must use effective contraception:
   a. Female subjects must be of non-childbearing potential or, if of childbearing potential, must have a negative urine or serum pregnancy test within 72 hours prior to taking study medication. If the urine test is positive or cannot be confirmed as negative, a serum pregnancy test will be required. The serum pregnancy test must be negative for the subject to be eligible. Non-childbearing potential is defined as (by other than medical reasons):
      ≥45 years of age and has not had menses for over 2 years
      Amenorrhoeic for >2 years without a hysterectomy and oophorectomy and a Follicle Stimulating Hormone (FSH) value in the postmenopausal range upon pretrial (Screening) evaluation
      Post hysterectomy, bilateral oophorectomy, bilateral salpingectomy or bilateral tubal ligation at least 6 weeks prior to Screening. Documented hysterectomy or oophorectomy must be confirmed with medical records of the actual procedure or confirmed by ultrasound. Tubal ligation must be confirmed with medical records of the actual procedure otherwise the subject must be willing to use two adequate barrier methods throughout the study, starting with the Screening visit through 120 days after the last dose of study therapy.
   Male subjects must agree to use an adequate method of contraception starting with the first dose of study therapy through 120 days after the last dose of study therapy.

Exclusion Criteria

A subject must be excluded from participating in the trial if he/she:

1. Has a pancreatic tumor other than adenocarcinoma, including: acinar cell carcinoma, pancreaticoblastoma, malignant cystic neoplasms, endocrine neoplasms, squamous cell carcinoma. Vater and periampullary duodenal or common bile duct malignancies.
2. Subjects with a bowel obstruction.
3. Has an active infection requiring systemic therapy or has an uncontrolled infection.
4. Has a known additional malignancy that is progressing or requires active treatment. Exceptions are adequately treated basal cell or squamous cell carcinoma that has undergone potentially curative therapy or carcinoma in situ of the cervix.
5. Has an underlying medical condition that would preclude study participation.
6. Has a disease that is suitable for therapy administered with curative intent.
7. Is currently participating and receiving study therapy or has participated in a study of an investigational agent and received study therapy or used an investigational device within 4 weeks of the first dose of treatment.
8. Has a diagnosis of immunodeficiency or is receiving systemic steroid therapy or any other form of immunosuppressive therapy within 7 days prior to the first dose of trial treatment.
9. Has had a prior anti-cancer monoclonal antibody (mAb) within 4 weeks prior to study Day 1 or who has not recovered (i.e., ≤Grade 1 or at Baseline) from AE due to agents administered more than 4 weeks earlier.
10. Has had prior chemotherapy, targeted small molecule therapy, or radiation therapy within 2 weeks prior to study Day 1 or has not recovered (i.e., ≤Grade 1 or at Baseline) from AE due to a previously administered agent.
11. An active autoimmune disease that has required systemic treatment in the 2 years preceding the study (i.e., with the use of disease-modifying agents, corticosteroids or immunosuppressive drugs).
12. Has received transfusions of blood products (including platelets or red blood cells) or administration of colony stimulating factors (including Granulocyte Colony Stimulating Factor [G-CSF], GM-CSF or recombinant erythropoietin) within 4 weeks prior to study Day 1.
13. Has a history of (non-infectious) pneumonitis that required steroids or current pneumonitis.
14. Has a history of interstitial lung disease.
15. O2 saturation <92% (on room air).
16. Has unstable angina, new onset angina within the last 3 months, myocardial infarction within the last 6 months, and current congestive heart failure New York Heart Association Class III or higher. Has ventricular arrhythmias or uncontrolled blood pressure, or severe arterial thromboembolic events less than 6 months prior to study initiation.
17. Has a history or current evidence of any condition, therapy, or laboratory abnormality that might confound the results of the trial, interfere with the subject's participation for the full duration of the trial, or is not in the best interest of the subject to participate, in the opinion of the treating Investigator.
18. Has known psychiatric or substance abuse disorders that would interfere with cooperation with the requirements of the trial.
19. Is pregnant or breastfeeding or expecting to conceive or father children within the projected duration of the trial, starting with the Screening visit through 120 days after the last dose of trial treatment. Women with a positive pregnancy test within 72 hours from Baseline.
20. Has received prior therapy with an anti-PD-1, anti-PD-L1, or anti-PD-L2 agent or if the subject has previously participated in Merck MK-3475 clinical trials.
21. Has a positive HIV test at Screening or at any time prior to Screening. Patients without a prior positive HIV test result will undergo an HIV test at Screening, unless not permitted per local regulations.
22. Has known active Hepatitis B (defined as having a positive Hepatitis B surface antigen (HBsAg) test at Screening) or Hepatitis C (defined as having a positive HCV antibody test or a positive HCV RNA test at Screening).
23. Has known history of Chronic Hepatitis B or C.
24. Has received a live vaccine within 30 days of the planned start of study therapy. Seasonal flu vaccines that do not contain live virus are permitted.
25. Has known active central nervous system (CNS) metastases and/or carcinomatous meningitis. Note: Subjects with previously treated brain metastases may participate provided they are stable (without evidence of progression by imaging using the identical imaging modality for each assessment, either MRI or computerized tomography (CT) scan, for at least four weeks prior to the first dose of trial treatment and any neurologic symptoms have returned to baseline), have no evidence of new or enlarging brain metastases, and are not using steroids for at least 14 days prior to trial treatment. This exception does not include carcinomatous meningitis which is excluded regardless of clinical stability.

26. Has severe hypersensitivity (≥Grade 3) to pembrolizumab and/or any of its excipients.

27. Has clinical ascites requiring treatment.

Subject Identification

Each consented subject receives a unique subject number that is used to identify the subject for all procedures that occur from Screening throughout the end of study or until the subject terminates from the study. Each subject is assigned only one subject number. Subject numbers must not be re-used for different subjects.

Any subject who is screened multiple times will retain the original subject number assigned at the initial Screening visit. A single subject may not be assigned more than one subject number.

Screening Failures

Subjects who fail to meet the entrance criteria at any stage during the Screening period are defined as screening failures.

Removal, Replacement, or Early Withdrawal of Subjects from Therapy or Assessment Subjects are free to discontinue the study drugs and/or their participation in the study at any time and without prejudice to further treatment. The Investigator must withdraw any subject from the study if that subject requests to be withdrawn, or if it is determined that continuing in the study would result in a significant safety risk to the subject. Patients can terminate the study treatment early (i.e. before two years) in the case of CR. Subjects that discontinue the study drug will continue to participate in the survival follow-up of the study for up to 5 years, unless they withdrew their consent to continue their participation in the study as well.

Subjects withdrawn from the study prior to the Baseline visit or prior to first injection of any of the study drugs will be replaced.

If a subject discontinues from the trial during the DLT evaluation period for any reason other than safety, a replacement subject may be enrolled if deemed appropriate to reach the target number for DLT assessment. Subjects who discontinued the trial during the DLT period because of progression will not be considered for DLT assessment; however, they will be counted as having progressed for the efficacy analysis. The replacement subject will be assigned a unique treatment/number.

The subject's use of study drug may be discontinued for any of the following reasons:
Toxicity
Death
Request of regulatory agency
Sponsor request
Primary care physician or Investigator request: Investigator decides that withdrawal from the study is in the best interest of the subject
Withdrawal of consent by subject
Disease Progression
Female subject who becomes pregnant
Lost to follow-up
Subject is non-compliant with study procedures/study protocol
Other Handling of Withdrawals If a subject is withdrawn from the study, every effort should be made to determine the reason. This information will be recorded on the subject's Case Report Form (CRF). All subjects who withdraw from the study prematurely, regardless of cause, should undergo all Early Discontinuation Study Visit procedures, safety follow-up visit and continue the long-term follow-up for survival.

If withdrawal is caused by an AE that the Investigator considers may be related to the study drug, the AE will be reported to the institutional review board/independent ethics committee (IRB/IEC) as per local guidelines if required.

All AEs will be followed up with appropriate medical management until the outcome is determined or stabilized, according to the Investigator's clinical judgment. All follow-up information will be recorded in the subject's CRF until resolution of the AE.

Discontinuation of Study Therapy after CR

Discontinuation of study drugs may be considered for subjects who have attained a confirmed CR, that:
Have been treated for at least 24 weeks with the combination therapy and
Received at least two treatment cycles of combination therapy beyond the date when the initial CR was declared.

Example 4

Treatment Period

The treatment period is comprised of two periods:
Monotherapy period: BL-8040 administered daily on Days 1-5.
Combination therapy:
Chemotherapy: Onivyde®/5-FU/LV every 2 weeks, pembrolizumab once every 3 weeks and BL-8040 twice a week.

Monotherapy

This period begins immediately after Baseline, preferably on the day of the Baseline assessments and will last for one week. During this period, BL-8040 is administered daily on Days 1 to 5. Pre-medication with systemic antihistamines is recommended in order to minimize the occurrence of BL-8040 related local injection site reactions and/or systemic reactions.

Week 1 (Days 1-5) Procedures

1. Review of AEs at each visit.
2. Prior and concomitant medications.
3. CBC with differential, daily on Days 1-5 pre-dose and 4 hr (±2 hr) post-dose on Day 1 and 5.
4. Blood for immunophenotyping by FACS on Day 1 and 5 pre-dose and 4 hr (±2 hr) post-dose.
5. Directed PE on Day 5 (+ up to 3 days, but before the beginning of the combination period).
6. Vital signs Day 5 pre-dose of BL-8040, post-dose assessment maybe collected upon Investigator decision.
7. 12 lead ECG.
8. Blood for CA 19-9 and CEA on Day 5 (+ up to 3 days, but before the beginning of the combination period).
9. Blood for CXCR4 and PD-1 expression on Day 1 and 5 pre-dose and 4 hr (±2 hr) post-dose.
10. Tumor tissue collection from metastasis (biopsy) for assessment on Day 5 (+ up to 4 days, but before the beginning of the combination period).
11. Tumor imaging assessment on Day 5 (+ up to 4 days, but before the beginning of the combination period).
12. Blood for cells, DNA and RNA for biomarker correlative studies on Day 5 (+ up to 3 days, but before the beginning of the combination period).

13. Serum for biomarker correlative studies on Day 5 (+ up to 3 days, but before the beginning of the combination period (Immune cells).

Combination Treatment

Cycles are defined according to the pembrolizumab three-week-cycle schedule of treatment.

From Day 8 (+ up to 4 days) subjects will begin a combination period consisting of treatment with:
  IV Onivyde® 70 mg/m² over 90 minutes, followed by IV LV 400 mg/m² over 30 minutes, followed by IV 5-FU 2400 mg/m² over 46 hours, every 2 weeks.
  IV Pembrolizumab 200 mg once every three weeks.
  Beginning on Day 10, SC BL-8040 1.25 mg/kg twice a week and at least 24 hours after chemotherapy dosing.

The combination therapy continues until progression, clinical deterioration or early Termination.

Pre-medication with systemic antihistamines is recommended in order to minimize the occurrence of BL-8040 related local injection site reactions and/or systemic reactions.

The following assessments should be done at each cycle (time window will be ±3 days unless otherwise specified):
1. Review prior and concomitant medications at all visits.
2. Review of AEs at all visits.
3. Directed PE on Day 1 pre-dose beginning in Cycle 2.
4. Vital signs will be assessed on Day 1 of each cycle before study drug administration, post-dose vital sign assessment may be collected upon Investigator decision.
5. Weight will be assessed at the beginning of each week during the combination treatment period before the first injection of the week. BL-8040 dose will be adjusted accordingly.
6. ECOG performance status on Day 1 of each cycle.
7. Chemistry panel on Day 1 of each cycle before study drug administration.
8. Treatment administration.
   i. BL-8040 administration two times a week.
   ii. Pembrolizumab administration on Day 1 of each 3-week cycle.
   iii. Onivyde®/5-FU/LV every 2 weeks.

The following assessments should be done at specific cycles (time window is ±3 days unless otherwise specified):
1. CBC with differential
a. Cycle 1:
  Pre-dose for the first three doses of BL-8040 for assessment of WBC (no window is allowed for CBC prior to BL-8040 injection). Further assessments should be performed as deemed necessary.
  4 hr (±2 hr) post-injection for the first three doses of BL-8040 for assessment of WBC.
b. Cycle 2 and Onward:
  Pre-dose of each BL-8040 in each treatment cycle for assessment of WBC (no window is allowed for CBC prior to BL-8040 injection). Further assessments are performed as deemed necessary.
2. 12 lead ECG on Day 1 of Cycle 1 pre-dose and 4 hr (±2 hr) after the combination treatment.
3. T3 (total or free), free T4 and TSH on Day 1 of Cycle 1 and thereafter on Day 1 of every two cycles beginning in Cycle 2 prior to dosing.
4. Pregnancy test—serum or urine every two cycles beginning in Cycle 2.
5. Blood for CA 19-9 and CEA on Day 1 of every two cycles beginning in Cycle 2.
6. Blood for immunophenotyping by FACS:
  on Day 15 of Cycle 1 and Day 21 of Cycle 2.
7. Blood for CXCR4 and PD-1 expression on Day 15 of Cycle 1 and Day 21 of Cycle 2.
8. Blood for DNA and RNA for biomarker correlative studies:
  a. Blood for cells, DNA and RNA correlative studies are collected on Cycle 1/Day 15 prior to the second cycle of chemotherapy and on Day 21 of every two cycles beginning in Cycle 3.
9. Tumor imaging assessment is done at the end of Cycle 2, and then every 3 cycles up to one year of treatment (Cycle 17) and then every 4 cycles until end of Cycle 34/Termination visit (two years of treatment).
10. Serum for biomarker correlative studies will be collected on Cycle 1/Day 15 prior to the second cycle of chemotherapy and on Day 21 of every two cycles beginning in Cycle 3 (immune cells, receptor occupancy, CA19-9).

A more specific embodiment is outlined below:

BL-8040

Trial treatment with BL-8040 will be administrated by SC injection of 1.25 mg/kg daily as monotherapy for 1 week, beginning on Day 1 daily through Day 5. Subjects will receive once daily SC injections of BL-8040 in the morning. Pre-medication with systemic antihistamines with or without analgesics is recommended in order to minimize the occurrence of BL-8040 related local injection site reactions and/or systemic reactions.

The BL-8040 injection site will be rotated to minimize the severity of any local injection site reactions. If the dose volume after reconstitution is higher than 2 ml, injections should be split in order to have less than 2 ml per injection; at the discretion of the Investigator, a single-dose administration may be split and injected into more than one site. The same instructions are applicable for combination period of the study.

BL-8040 injections will be skipped in case of a significant increase in WBC (WBC>60,000/μL) measured prior to administration of the next BL-8040 injection and/or evidence of leukostasis. BL-8040 treatment will resume provided there are no signs of leukostasis and or the WBC decrease to values ≤60,000/μL.

After monotherapy, BL-8040 will be administered as part of the combination treatment with pembrolizumab in cycles of three-week duration. Dosing will be as follow:
  During the combination period, BL-8040 will be administered two times a week on non-consecutive days, 48 hours apart and at least 24 hours after chemotherapy, as a SC injection during the morning.

Blood draw and other assessments should be completed before BL-8040 administration. Treatment with BL-8040 can be delayed, provided that upon resuming treatment, it will continue with the same schedule as defined within the protocol, i.e. missed doses will not be made up. In case more than two consecutive doses are skipped during the monotherapy period or more than three consecutive doses (a week of treatment) during the combination period, the Investigator will assess the risk-benefit and decide whether the subject can continue the study participation. The reason for interruption should be documented in the subject's study record.

Pembrolizumab

Treatment with pembrolizumab will begin following the monotherapy period and as a part of the combination therapy. During the combination period pembrolizumab will be administered as a dose of 200 mg using a 30-minute IV infusion on Day 1 of each 3-week treatment cycle after all procedures and assessments have been completed. Pembrolizumab may be administered up to 3 days before or after the scheduled Day 1 of each cycle due to administrative reasons.

Pembrolizumab will be administered as a dose of 200 mg using a 30-minute IV infusion. Every effort should be made to target infusion timing to be as close to 30 minutes as possible. However, given the variability of infusion pumps, a window between −5 minutes and +10 minutes is permitted (i.e., infusion time is 30 minutes−5 min/+10 min).

When pembrolizumab is provided in the same day of BL-8040, BL-8040 administration 1 hour (±0.5 hour) after the end of the pembrolizumab infusion.

When pembrolizumab is provided in the same day of the chemotherapy, pembrolizumab should be administered first, followed by the chemotherapy.

Dosing interruptions are permitted in the case of medical/surgical events or logistical reasons (i.e. elective surgery, unrelated medical events, subject vacation, holidays) not related to study therapy. Subjects should be placed back on study therapy within 3 weeks of the scheduled interruption. The reason for interruption should be documented in the subject's study record.

Onivyde/5-FU/LV

Onivyde should be administered prior to LV and 5-FU. Onivyde 70 mg/m$^2$ as an IV infusion over 90 minutes, followed by LV 400 mg/m$^2$ IV over 30 minutes, followed by 5-FU 2400 mg/m$^2$ IV over 46 hours, every 2 weeks. Patients homozygous for the UGT1A1*28 allele will initiate Onivyde® at 50 mg/m$^2$, and the dose can be increased if tolerated at later cycles.

Example 5

Safety Follow-Up Visit

After Termination/Early Termination visit, a safety follow-up visit is performed approximately 30 days after the last dose of the last study drug (or within 7 days prior to initiation of a new anti-cancer treatment, whichever comes first). The subject is monitored for AEs up to the safety follow-up visit or until resolution of toxicity to Grade 0-1 or AE stabilization, whichever occurs later. SAEs should be reported when occur within 90 days and pregnancies when occurred within 120 days of study termination, or, in both cases, 30 days following cessation if a new anti-cancer therapy is initiated.

The following assessment is performed during this visit.
1. Review of AEs
2. Review prior and concomitant medications
3. Post-study anti-cancer therapy received
4. CBC with differential
5. Chemistry Panel
6. T3 (total or free), freeT4, TSH
7. 12 lead ECG Long-Term Follow-Up of Survival All subjects will be contacted by phone every 12 weeks (±4 weeks) in order to assess their survival status regardless of the reason for discontinuation (i.e. early termination [ET] or after two years). This Follow-up will continue for up to 5 years unless they withdrew their consent to continue their participation in the study. During these phone calls, subjects will be asked to provide, among others, an update about disease status and post-study anti-cancer therapy received. All the data will be collected and entered within the CRF as well.

Unscheduled Visit

An unscheduled visit may be performed at any time during the study at the subject's request or as deemed necessary by the Investigator. The date and reason for the unscheduled visit will be recorded. AE monitoring and concomitant medication recording will be performed by the Investigator. Other procedures and evaluations will be completed as deemed necessary by the Investigator and may include (but are not limited to) laboratory safety tests, vital signs and physical examination.

Safety Assessments

Safety assessments will be based on changes from Baseline of clinical signs and symptoms reported by the subject or observed by the Investigator, including AEs, concomitant medication use, treatment compliance, tolerability (e.g. dropouts due to AEs), vital signs, ECGs, physical examination and laboratory safety assessments.

Adverse Events (AEs)

Adverse Events (AEs) will be assessed at all study visits throughout the study.

Any new AE that occurs between scheduled assessment visits should be brought to the attention of the Investigator and recorded in the subject's medical file and on the appropriate CRF page.

AEs will be reported and graded in accordance with the latest National Cancer Institute Common Terminology Criteria for Adverse Events (NCI-CTCAE) version (currently version 4.03) and coded by Data Management using the latest version of Medical Dictionary for Regulatory Activities (MedDRA).

Concomitant Medications

Concomitant medication use will be recorded from Baseline through all study visits.

Vital Signs, Height and Weight

Vital signs will be measured at Screening, at Baseline and pre-dose on Day 5 of the monotherapy treatment. Post-dose assessment may be performed as deemed necessary by the Investigator. During the combination period, vital signs will be assessed on Day 1 of each cycle before study drug administration. Further assessment may be performed upon Investigator decision.

Vital signs will include blood pressure, pulse, oral temperature, $O_2$ saturation and respiration rate following a minimum of 5 minutes of rest as per standard practice. Significant findings noticed after the start of study drug which meet the definition of an AE must be recorded on the AE CRF module.

Height will be recorded only at Screening.

Weight will be recorded at Baseline and on at the beginning of each week (combination period) before dosing in order to calculate the BL-8040 dose.

Electrocardiogram

An ECG will be performed at the Screening and Baseline (Day 1 pre-dose) visits.

During the combination period, an ECG will be performed on Cycle 1/Day 1 pre-dose and 4 hours (±2 hours) after the last study drug administered. An ECG will be performed at the Termination visit and at any safety follow-up visit as well.

Additional ECGs will be performed at the discretion of the Investigator. The subject should rest for at least 10 minutes before the measurement is taken.

ECG printouts will be evaluated by the Investigator or designee, signed and dated and filed in the source documentation file. When potentially Clinically Significant findings are detected by the Investigator or designee; a cardiologist should be consulted for a definitive interpretation and appropriate treatment if required. All communications and diagnoses should be filed in the source documentation file. The Investigator/Investigator's designee/local cardiologist is responsible for determining whether the ECG findings are of clinical significance. All abnormalities shall be closely monitored until stabilized or resolved. Clinically significant finding should be reported within the AEs CRF page.

Physical Examination and Directed Physical Examination

A full PE will be conducted at Screening and at the time of discontinuation. The PE will include assessment of the following body systems: head, neck, thyroid, respiratory, cardiovascular, ophthalmologic, gastrointestinal, hepatic, endocrine/metabolic, musculoskeletal system, dermatological, lymph nodes, neurological system and, where appropriate, other body systems as indicated in the study schedule.

A directed PE will be conducted on Day 5 of the monotherapy period (±3 days but before the first dose of the combination) and on Day 1 of each cycle beginning at Cycle 2 (±3 days but before the first dose of the combination of Cycle 2) (FIG. 1). During a directed PE, particular attention should be focused on identifying possibly drug-related AEs and managing these AEs effectively.

Information about the PE must be present. Significant findings that are present prior to the start of study drug must be included in the Relevant Medical History/Current Medical Conditions CRF. Significant findings made after the start of study drug which meet the definition of an AE must be recorded on the AE CRF module.

Laboratory Safety Assessments

All clinical laboratory safety assessments, listed below, will be performed by local laboratories at Screening and at different time points during the monotherapy and combination treatment depending on the specific assessment. Pre-dose laboratory procedures may be conducted up to 4 hours prior to dosing.

Laboratory safety sampling will include the parameters listed below.

Laboratory tests for hematology, chemistry, urinalysis and others are specified in Table 2.

important by the Investigator will be reported as AEs in the AE CRF module. A laboratory abnormality will not be considered an AE unless:
 Intervention is required
 Changes in dose are required (decrease, discontinued, interrupted)
 Other treatment/therapy is required
 Associated with other diagnoses Example 6

Efficacy Assessments
Imaging Assessment

Imagining is used for assessment of response. For example, CT or MRI may be used. The same imaging method should be used throughout the treatment for each subject.

According to a specific embodiment, the imaging assessment can be done at:
 Time for subject selection to the treatment.
 End of Monotherapy period, Day 5.
 Combination treatment at the end of Cycle 2 and then every 3 cycles up to one year of treatment (Cycle 17) and then every 4 cycles until end of treatment.

According to a specific embodiment, RECIST 1.1 is adapted to account for the unique tumor response characteristics seen with treatment of immunotherapeutic agents. Agents such as pembrolizumab and BL-8040 may produce antitumor effects by potentiating endogenous cancer-specific immune responses. The response patterns seen with such an approach may extend beyond the typical time course of responses seen with cytotoxic agents and can manifest a clinical response after an initial increase in tumor burden or even the appearance of new lesions:

TABLE 2

Laboratory Tests

| Hematology | Chemistry | Urinalysis | Other |
| --- | --- | --- | --- |
| Hematocrit | Albumin | Blood | FSH |
| Hemoglobin | Alkaline phosphatase | Glucose | Serum or urine pregnancy test |
| Platelet count | Alanine aminotransferase (ALT) | Protein | Hepatitis B Surface Antigen [HBsAg] reactive |
| WBC (total and differential) | Aspartate aminotransferase (AST) | Specific gravity | Hepatitis C (e.g., HCV RNA [qualitative]) |
| RBC | Calcium | Microscopic examination | HIV1 and 2 |
| | Chloride | | TSH, T3 (free or total), and freeT4 |
| | Creatinine | | PT/INR and aPTT |
| | Glucose | | |
| | Phosphorus | | |
| | Potassium | | |
| | Sodium | | |
| | Total Bilirubin | | |
| | Direct Bilirubin | | |
| | Total protein | | |
| | Blood Urea Nitrogen | | |

A serum pregnancy test, if applicable, will be collected at Baseline and performed at the local laboratory.

Laboratory safety test abnormalities that arise after study drug administration will be repeated as clinically indicated until the values return to normal or until the etiology has been determined and the condition considered stable. Abnormal laboratory test results that are considered to be clinically If radiologic imaging verifies initial progressive disease, tumor assessment should be repeated ≥4 weeks later in order to confirm progressive disease with the option of continuing treatment per below.
 If repeat imaging shows less than a 20% increase in tumor burden compared to nadir, stable or improved previous new lesion (if identified as cause for initial progressive disease), and stable/improved non-target lesions (if identified as cause for initial progressive disease), treatment may be continued/resumed.

If repeat imaging confirms progressive disease due to any of the scenarios list below, subjects are discontinued from therapy.

In determining whether or not the tumor burden has increased or decreased, all target lesions as well as non-target lesions are considered.

Scenarios where progressive disease is confirmed at repeat imaging:
  Tumor burden remains increased by ≥20% and at least 5 mm absolute increase compared to nadir
  Non-target lesions resulting in initial progressive disease is worse (qualitative)
  New lesion resulting in initial progressive disease is worse (qualitative)
  Additional new lesion(s) since last evaluation In subjects who have initial evidence of radiological progressive disease, it is at the discretion of the treating physician whether to continue a subject on treatment until repeat imaging is obtained. This clinical judgment decision should be based on the subject's overall clinical condition, including performance status, clinical symptoms, and laboratory data. Subjects may continue to receive treatment while waiting for confirmation of progressive disease if they are clinically stable as defined by the following criteria:
  Absence of signs and symptoms indicating disease progression
  No decline in ECOG performance status
  Absence of rapid progression of disease
  Absence of progressive tumor at critical anatomical sites (e.g., cord compression) requiring urgent alternative medical intervention When feasible, subjects should not be discontinued until progression is confirmed. This allowance to continue treatment despite initial radiologic progression takes into account the observation that some subjects can have a transient tumor flare in the first few months after the start of immunotherapy, but with subsequent disease response. Subjects that are deemed clinically unstable are not required to have repeat imaging for confirmation of progressive disease.

If the physician assesses disease progression and the subject is clinically stable (described above), it is at the discretion of the physician to continue to treat and image the subject at least 4 weeks after the first tumor imaging indicating progressive disease. irRECIST would then be followed by the physician to determine if the follow-up tumor imaging confirms progressive disease. Subjects who have unconfirmed disease progression may continue on treatment and follow the regular imaging schedule intervals until progression is confirmed, provided they have met the conditions detailed above.

irRECIST Assessment of Disease

As noted above, if tumor imaging shows initial disease progression, the site may elect to continue treatment, repeat imaging ≥4 weeks later and assess tumor response or confirmed progression per irRECIST.

Planned Biopsy Analysis

According to a specific embodiment, biopsy can be performed at Screening and will be assessed for: tumor mutation burden (TMB), PD-L1 and DNA mismatch repair status.

Blood Sampling and Processing

Samples are collected for safety and efficacy analysis, anti-drug antibodies titer and determination of BL-8040 plasma concentrations.

Example 7

Identity of Investigational Product
BL-8040

BL-8040 is a highly selective CXCR4 antagonist co-developed by Biokine Therapeutics, Ltd. and BioLineRx Ltd. as a novel investigational therapy for the treatment of cancer.

BL-8040, a white to off-white powder synthetic polypeptide, is freely soluble in water and in 0.45% Sodium Chloride (half normal saline). It is manufactured in accordance with current Good Manufacturing Practice (cGMP) by Bio-Connection B.V. (previously MSD), Kloosterstraat 9, 5349 AB OSs, Netherlands.

Pembrolizumab

Pembrolizumab (MK-3475) Solution for Infusion is a sterile, non-pyrogenic aqueous solution supplied in single-use Type I glass vial containing 100 mg/4 mL of pembrolizumab (MK-3475). The product is preservative-free solution which is essentially free of extraneous particulates.

Chemotherapy: Onivyde®/5-FU/LV

Onivyde is an injection: 43 mg/10 mL irinotecan free base as a white to slightly yellow, opaque, liposomal dispersion in a single-dose vial.

Fluorouracil injection is supplied as a pharmacy bulk package as a vial containing 2.5 g/50 mL (50 mg/mL) fluorouracil.

Leucovorin Calcium for injection is supplied as a sterile lyophilized powder. The 350 mg vial is preservative-free. The inactive ingredient is sodium chloride 140 mg/vial for the 350 mg vial. Sodium hydroxide and/or hydrochloric acid are used to adjust the pH to approximately 8.1 during manufacture. 1 mg of leucovorin calcium contains 0.002 mmol of leucovorin and 0.002 mmol of calcium.

Example 8

A Phase 2a Trial to Assess the Safety and Efficacy of BL-8040 in Combination with Pembrolizumab and Chemotherapy in Patients with Metastatic Pancreatic Adenocarcinoma (PDAC)

Background

Current treatment options for PDAC are limited. While PD-1/PD-L1 antagonists have shown promising results in other cancer types, this approach has been ineffective in PDAC. In Cohort 1 of the COMBAT study, the dual combination of BL-8040 (CXCR4 inhibitor) and Pembrolizumab was safe and showed a promising 7.5 months median overall survival (OS) in $2^{nd}$ line patients (2L) patients (Hidalgo, A., et al., *A Phase 2a Trial to Assess the Safety and Efficacy of BL-8040 and Pembrolizumab in Patients with Metastatic Pancreatic Adenocarcinoma (PDAC)*. Annals of Oncology, 2018. 29: p. viii400-viii441). BL-8040 modifies the tumor microenvironment (TME) by increasing the level of effector CD8 cells that express Granzyme B as well as by decreasing the level of myeloid derived suppressor cells (MDSCs).

Based on these encouraging results, as well as preclinical data supporting the combination of BL-8040, Pembrolizumab and chemotherapy, the study was expanded to include a combination arm (Cohort 2) composed of BL-8040, Pembrolizumab and chemotherapy (Onivyde/5-FU/LV). Preliminary efficacy and safety data of BL-8040 in this expansion cohort is provided infra.

Methods

Phase 2a study, Cohort 2, treatment regimen consists of 5 days BL-8040 monotherapy followed by combination treatment of Onivyde/5-FU/LV every 2 weeks, Pembrolizumab every 3 weeks and BL-8040 twice a week. Eligibility criteria includes metastatic PDAC subjects with measurable disease by as described in Example 3 that have progressed following first-line treatment with gemcitabine-based chemotherapy.

Results

As of September 2019, 22 patients were enrolled, of which 15 are evaluable (i.e. received at least 1 dose of combination and have post baseline CT). Median age 68, ECOG≤1 and 60% males. 15 SAEs were reported by 10 patients. 2 subjects were discontinued due to SAEs. Best Response by RECISTv1.1 (Example 6) for the evaluable population showed 4 partial response (PR) and 8 stable disease (SD) patients, a total of 12 subjects with disease control out of 15. Median PFS and OS not yet reached. Notably, all patients with SD and PR had an initial increase in CA 19-9 followed by a decrease. Tumor shrinkage began during the transient increase of CA 19-9.

CONCLUSIONS

Preliminary data from the ongoing COMBAT study Cohort 2 with the triple combination of BL-8040, Pembrolizumab and chemo, show promising overall response rate (ORR) (4/15) and disease control rate (DCR) (12/15).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

REFERENCES

[1] Tamamura H, Hiramatsu K, Kusano S, Terakubo S, Yamamoto N, Trent J O, et al. Synthesis of potent CXCR4 inhibitors possessing low cytotoxicity and improved biostability based on T140 derivatives. Org Biomol Chem 2003; 1:3656-3662.

[2] Peled A, Petit I, Kollet O, Magid M, Ponomaryov T, Byk T, et al. Dependence of human stem cell engraftment and repopulation of NOD/SCID mice on CXCR4. Science 1999; 283:845-848.

[3] Beider K, Begin M, Abraham M, Wald H, Weiss I D, Wald O, et al. CXCR4 antagonist 4F-benzoyl-TN14003 inhibits leukemia and multiple myeloma tumor growth. Exp Hematol 2011; 39:282-292.

[4] Beider K, Darash-Yahana M, Blaier O, Koren-Michowitz M, Abraham M, Wald H, et al. Combination of imatinib with CXCR4 antagonist BKT140 overcomes the protective effect of stroma and targets CML in vitro and in vivo. Mol Cancer Ther 2014; 13:1155-1169.

[5] Tavor S, Weiss I, Beider K, Wald H, Eizenberg O, Pereg Y, et al. The CXCR4 Antagonist BL-8040 Efficiently Induces Apoptosis and Inhibits The Survival Of AML Cells. Blood 2013; 122:3939-3939.

[6] Abraham M, Wald H, Eizenberg O, Bulvik B, Tavor S, Beider K, et al. The CXCR4 Antagonist BL-8040 Synergizes with the FLT3 Inhibitor AC220 to Induce Apoptosis and Reduce Minimal Residual Disease of AML Cells in vivo. Haematologica, vol. 99, Ferrata Storti Foundation; 2014, p. 291-292.

[7] Disis M L. Immune regulation of cancer. J Clin Oncol Off J Am Soc Clin Oncol 2010; 28:4531-8. doi:10.1200/JCO.2009.27.2146.

[8] Dudley M E, Wunderlich J R, Yang J C, Sherry R M, Topalian S L, Restifo N P, et al. Adoptive cell transfer therapy following non-myeloablative but lymphodepleting chemotherapy for the treatment of patients with refractory metastatic melanoma. J Clin Oncol Off J Am Soc Clin Oncol 2005; 23:2346-57. doi: 10.1200/JCO.2005 0.00.240.

[9] Hunder N N, Wallen H, Cao J, Hendricks D W, Reilly J Z, Rodmyre R, et al. Treatment of metastatic melanoma with autologous CD4+ T cells against NY-ESO-1. N Engl J Med 2008; 358:2698-703. doi:10.1056/NEJMoa0800251.

[10] Greenwald R J, Freeman G J, Sharpe A H. The B7 family revisited. Annu Rev Immunol 2005; 23:515-48. doi:10.1146/annurev.immunol.23.021704.115611.

[11] Okazaki T, Maeda A, Nishimura H, Kurosaki T, Honjo T. PD-1 immunoreceptor inhibits B cell receptor-mediated signaling by recruiting src homology 2-domain-containing tyrosine phosphatase 2 to phosphotyrosine. Proc Natl Acad Sci USA 2001; 98:13866-71. doi: 10.1073/pnas.231486598.

[12] Zhang X, Schwartz J-CD, Guo X, Bhatia S, Cao E, Chen L, et al. Structural and functional analysis of the costimulatory receptor programmed death-1. Immunity 2004; 20:337-347.

[13] Chemnitz J M, Parry R V, Nichols K E, June C H, Riley J L. SHP-1 and SHP-2 associate with immunoreceptor tyrosine-based switch motif of programmed death 1 upon primary human T cell stimulation, but only receptor ligation prevents T cell activation. J Immunol Baltim Md 1950 2004; 173:945-54.

[14] Sheppard K-A, Fitz L J, Lee J M, Benander C, George J A, Wooters J, et al. PD-1 inhibits T-cell receptor induced phosphorylation of the ZAP70/CD3ζ signalosome and downstream signaling to PKC$\theta$eta$. FEBS Lett 2004; 574:37-41.

[15] Riley J L. PD-1 signaling in primary T cells. Immunol Rev 2009; 229:114-25. doi:10.1111/j.1600-065X.2009.00767.x.

[16] Parry R V, Chemnitz J M, Frauwirth K A, Lanfranco A R, Braunstein I, Kobayashi S V, et al. CTLA-4 and PD-1 receptors inhibit T-cell activation by distinct mechanisms. Mol Cell Biol 2005; 25:9543-53. doi:10.1128/MCB.25.21.9543-9553.2005.

[17] Francisco L M, Sage P T, Sharpe A H. The PD-1 pathway in tolerance and autoimmunity. Immunol Rev 2010; 236:219-42. doi:10.1111/j.1600-065X.2010.00923.x.

[18] Hirano F, Kaneko K, Tamura H, Dong H, Wang S, Ichikawa M, et al. Blockade of B7-H1 and PD-1 by monoclonal antibodies potentiates cancer therapeutic immunity. Cancer Res 2005; 65:1089-1096.

[19] Blank C, Brown I, Peterson A C, Spiotto M, Iwai Y, Honjo T, et al. PD-L1/B7H-1 inhibits the effector phase of tumor rejection by T cell receptor (TCR) transgenic CD8+ T cells. Cancer Res 2004; 64:1140-1145.

[20] Weber J. Immune checkpoint proteins: a new therapeutic paradigm for cancer—preclinical background: CTLA-4 and PD-1 blockade. Semin. Oncol., vol. 37, Elsevier; 2010, p. 430-439.

[21] Spranger S, Koblish H K, Horton B, Scherle P A, Newton R, Gajewski T F. Mechanism of tumor rejection with doublets of CTLA-4, PD-1/PD-L1, or IDO blockade involves restored IL-2 production and proliferation of CD8+ T cells directly within the tumor microenvironment. J Immunother Cancer 2014; 2:3.

[22] Curran M A, Montalvo W, Yagita H, Allison J P. PD-1 and CTLA-4 combination blockade expands infiltrating T cells and reduces regulatory T and myeloid cells within B16 melanoma tumors. Proc Natl Acad Sci 2010; 107: 4275-4280.

[23] Pilon-Thomas S, Mackay A, Vohra N, Mulé J J. Blockade of programmed death ligand 1 enhances the therapeutic efficacy of combination immunotherapy against melanoma. J Immunol 2010; 184:3442-3449.

[24] Strome S E, Dong H, Tamura H, Voss S G, Flies D B, Tamada K, et al. B7-H1 blockade augments adoptive T-cell immunotherapy for squamous cell carcinoma. Cancer Res 2003; 63:6501-6505.

[25] Nomi T, Sho M, Akahori T, Hamada K, Kubo A, Kanehiro H, et al. Clinical significance and therapeutic potential of the programmed death-1 ligand/programmed death-1 pathway in human pancreatic cancer. Clin Cancer Res 2007; 13:2151-2157.

[26] ONIVYDE™ (irinotecan liposome injection), for intravenous use. US Label 2015.

[27] Lamb Y N, Scott L J. Liposomal Irinotecan: A Review in Metastatic Pancreatic Adenocarcinoma. Drugs 2017; 77:785-92. doi:10.1007/s40265-017-0741-1.

[28] FLUOROURACIL injection, for intravenous use. US Label. 2016.

[29] Leucovorin calcium for injection 2001.

[30] Saif M W. Controversies in the adjuvant treatment of pancreatic adenocarcinoma. JOP J Pancreas 2007; 8:545-52.

[31] Bilimoria K Y, Bentrem D J, Ko C Y, Ritchey J, Stewart A K, Winchester D P, et al. Validation of the 6th edition AJCC Pancreatic Cancer Staging System: report from the National Cancer Database. Cancer 2007; 110:738-44. doi:10.1002/cncr.22852.

[32] Strobel O, Hartwig W, Hackert T, Hinz U, Berens V, Grenacher L, et al. Re-resection for isolated local recurrence of pancreatic cancer is feasible, safe, and associated with encouraging survival. Ann Surg Oncol 2013; 20:964-72. doi:10.1245/s10434-012-2762-z.

[33] Von Hoff D D, Ervin T, Arena F P, Chiorean E G, Infante J, Moore M, et al. Increased survival in pancreatic cancer with nab-paclitaxel plus gemcitabine. N Engl J Med 2013; 369:1691-703. doi:10.1056/NEJMoa1304369.

[34] Wang-Gillam A, Li C-P, Bodoky G, Dean A, Shan Y-S, Jameson G, et al. Nanoliposomal irinotecan with fluorouracil and folinic acid in metastatic pancreatic cancer after previous gemcitabine-based therapy (NAPOLI-1): a global, randomised, open-label, phase 3 trial. Lancet Lond Engl 2016; 387:545-57. doi:10.1016/50140-6736(15)00986-1.

[35] Naito Y, Saito K, Shiiba K, Ohuchi A, Saigenji K, Nagura H, et al. CD8+ T cells infiltrated within cancer cell nests as a prognostic factor in human colorectal cancer. Cancer Res 1998; 58:3491-4.

[36] Galon J, Costes A, Sanchez-Cabo F, Kirilovsky A, Mlecnik B, Lagorce-Pagès C, et al. Type, density, and location of immune cells within human colorectal tumors predict clinical outcome. Science 2006; 313:1960-4. doi:10.1126/science.1129139.

[37] Zhang L, Conejo-Garcia J R, Katsaros D, Gimotty P A, Massobrio M, Regnani G, et al. Intratumoral T cells, recurrence, and survival in epithelial ovarian cancer. N Engl J Med 2003; 348:203-13. doi:10.1056/NEJMoa020177.

[38] Sato E, Olson S H, Ahn J, Bundy B, Nishikawa H, Qian F, et al. Intraepithelial CD8+ tumor-infiltrating lymphocytes and a high CD8+/regulatory T cell ratio are associated with favorable prognosis in ovarian cancer. Proc Natl Acad Sci USA 2005; 102:18538-43. doi: 10.1073/pnas.0509182102.

[39] Feig C, Jones J O, Kraman M, Wells R J B, Deonarine A, Chan D S, et al. Targeting CXCL12 from FAP-expressing carcinoma-associated fibroblasts synergizes with anti-PD-L1 immunotherapy in pancreatic cancer. Proc Natl Acad Sci USA 2013; 110:20212-7. doi: 10.1073/pnas.1320318110.

[40] Joyce J A, Fearon D T. T cell exclusion, immune privilege, and the tumor microenvironment. Science 2015; 348:74-80. doi:10.1126/science.aaa6204.

[41] Beider K, Begin M, Abraham M, Wald H, Weiss I D, Wald O, et al. CXCR4 antagonist 4F-benzoyl-TN14003 inhibits leukemia and multiple myeloma tumor growth. Exp Hematol 2011; 39:282-92.

[42] Beider K, Ribakovsky E, Abraham M, Wald H, Weiss L, Rosenberg E, et al. Targeting the CD20 and CXCR4 pathways in non-hodgkin lymphoma with rituximab and high-affinity CXCR4 antagonist BKT140. Clin Cancer Res Off J Am Assoc Cancer Res 2013; 19:3495-507. doi:10.1158/1078-0432.CCR-12-3015.

[43] Zhang Y, Patel S, Abdelouahab H, Wittner M, Willekens C, Shen S, et al. CXCR4 inhibitors selectively eliminate CXCR4-expressing human acute myeloid leukemia cells in NOG mouse model. Cell Death Dis 2012; 3:e396.

[44] Fahham D, Weiss I D, Abraham M, Beider K, Hanna W, Shlomai Z, et al. In vitro and in vivo therapeutic efficacy of CXCR4 antagonist BKT140 against human non-small cell lung cancer. J Thorac Cardiovasc Surg 2012; 144: 1167-1175.el. doi:10.1016/j.jtcvs.2012.07.031.

[45] Tamamura H, Hori A, Kanzaki N, Hiramatsu K, Mizumoto M, Nakashima H, et al. T140 analogs as CXCR4 antagonists identified as anti-metastatic agents in the treatment of breast cancer. FEBS Lett 2003; 550:79-83.

[46] Von Hoff D D, Ervin T, Arena F P, Chiorean E G, Infante J, Moore M, et al. Increased survival in pancreatic cancer with nab-paclitaxel plus gemcitabine. N Engl J Med 2013; 369:1691-703.

[47] Hidalgo M M, Epelbaum R, Semenisty V, Geva R, Golan T, Borazanci E H, et al. Evaluation of pharmacodynamic (PD) biomarkers in patients with metastatic pancreatic cancer treated with BL-8040, a novel CXCR4 antagonist. J Clin Oncol 2018; 36:88-88. doi:10.1200/JCO.2018.36.5_suppl.88.

[48] Emens L A, Middleton G. The interplay of immunotherapy and chemotherapy: harnessing potential synergies. Cancer Immunol Res 2015; 3:436-43. doi:10.1158/2326-6066.CIR-15-0064.

[49] Khoja L, Kibiro M, Metser U, Gedye C, Hogg D, Butler M O, et al. Patterns of response to anti-PD-1 treatment: an exploratory comparison of four radiological response criteria and associations with overall survival in metastatic melanoma patients. Br J Cancer 2016; 115:1186-92. doi:10.1038/bjc.2016.308.

[50] Wang-Gillam A, Li C-P, Bodoky G, Dean A, Shan Y-S, Jameson G, et al. Nanoliposomal irinotecan with fluorouracil and folinic acid in metastatic pancreatic cancer after previous gemcitabine-based therapy (NAPOLI-1): a global, randomised, open-label, phase 3 trial. Lancet Lond Engl 2016; 387:545-57. doi:10.1016/S0140-6736(15)00986-1.

What is claimed is:

1. A method of treating metastatic pancreatic adenocarcinoma in a subject in need thereof, the method comprising administering to the subject a therapeutically effective amount of each of a peptide set forth in SEQ ID NO: 1, an anti PD-1 antibody and a chemotherapy, thereby treating the metastatic pancreatic adenocarcinoma, wherein administering comprises a monotherapy period with said peptide followed by a combination therapy with said peptide, said anti PD-1 antibody and said chemotherapy, wherein said subject is post first-line treatment against said metastatic pancreatic adenocarcinoma, wherein said chemotherapy comprises irinotecan, fluorouracil (5-FU) and leucovorin (LV), wherein said anti-PD-1 antibody is pembrolizumab and wherein said combination therapy with said chemotherapy and said anti PD-1 is initiated on Day 8, and wherein said first-line treatment comprises a gemcitabine-based chemotherapy.

2. The method of claim 1, wherein said combination therapy is repeated every 2 weeks with said chemotherapy and every 3 weeks with said anti PD-1.

3. The method of claim 1, wherein said monotherapy is performed on Days 1-5, daily.

4. The method of claim 3, wherein said treatment further comprises an anti-histamine and optionally analgesics.

5. The method of claim 1, wherein said combination therapy with said peptide is initiated on Day 10 two times a week on non-consecutive days, 48 hours apart.

6. The method of claim 1, wherein said chemotherapy is administered intravenously.

7. The method of claim 1, wherein said irinotecan is liposome-encapsulated.

8. The method of claim 1, wherein said peptide is administered subcutaneously (SC).

9. The method of claim 1, wherein said peptide is administered at a dose of 1.25 mg/kg.

10. The method of claim 1, wherein said anti PD-1 is administered intravenously (IV).

11. The method of claim 1, wherein said anti PD-1 is administered at a dose of 200 mg.

* * * * *

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 1

Xaa Arg Xaa Cys Tyr Xaa Lys Xaa Pro Tyr Arg Xaa Cys Arg
1               5                   10
```